United States Patent
Boiteau et al.

(10) Patent No.: US 8,299,259 B2
(45) Date of Patent: Oct. 30, 2012

(54) 4-(AZACYCLOALKYL)BENZENE-1,3-DIOL COMPOUNDS AS TYROSINASE INHIBITORS, PROCESS FOR THE PREPARATION THEREOF AND USE THEREOF IN HUMAN MEDICINE AND IN COSMETICS

(75) Inventors: Jean-Guy Boiteau, Valbonne (FR); Karine Bouquet, St Laurent du Var (FR); Sandrine Talano, Vence (FR); Corinne Millois Barbuis, Saint Raphael (FR)

(73) Assignee: Galderma Research & Development, Biot (FR)

( * ) Notice: Subject to any disclaimer, the term of this patent is extended or adjusted under 35 U.S.C. 154(b) by 0 days.

(21) Appl. No.: 13/131,363

(22) PCT Filed: Dec. 2, 2009

(86) PCT No.: PCT/EP2009/066268
§ 371 (c)(1),
(2), (4) Date: Sep. 12, 2011

(87) PCT Pub. No.: WO2010/063774
PCT Pub. Date: Jun. 10, 2010

(65) Prior Publication Data
US 2011/0311466 A1     Dec. 22, 2011

Related U.S. Application Data

(60) Provisional application No. 61/193,460, filed on Dec. 2, 2008.

(30) Foreign Application Priority Data
Dec. 2, 2008  (FR) .................................... 08 58207

(51) Int. Cl.
C07D 211/06     (2006.01)
C07D 295/00     (2006.01)
(52) U.S. Cl. ....................................... 546/226; 548/531
(58) Field of Classification Search ............... 546/226; 548/531
See application file for complete search history.

(56) References Cited

FOREIGN PATENT DOCUMENTS
WO     2006133784 A     12/2006

OTHER PUBLICATIONS
International Search Report dated Feb. 19, 2010 issued in International Application No. PCT/EP2009/066268.

*Primary Examiner* — Janet Andres
*Assistant Examiner* — John Mabry
(74) *Attorney, Agent, or Firm* — SNR Denton US LLP

(57) ABSTRACT

4-(azacycloalkyl)benzene-1,3-diol compounds are described corresponding to general formula (I) below:

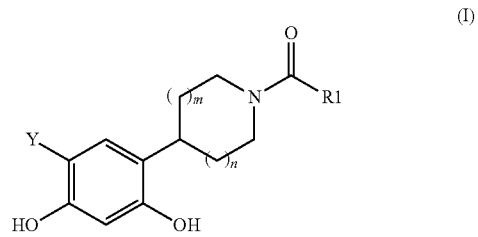

Also described, are compositions including the same, processes for preparation thereof and uses thereof in pharmaceutical or cosmetic compositions to treat pigmentary disorders.

4 Claims, 1 Drawing Sheet

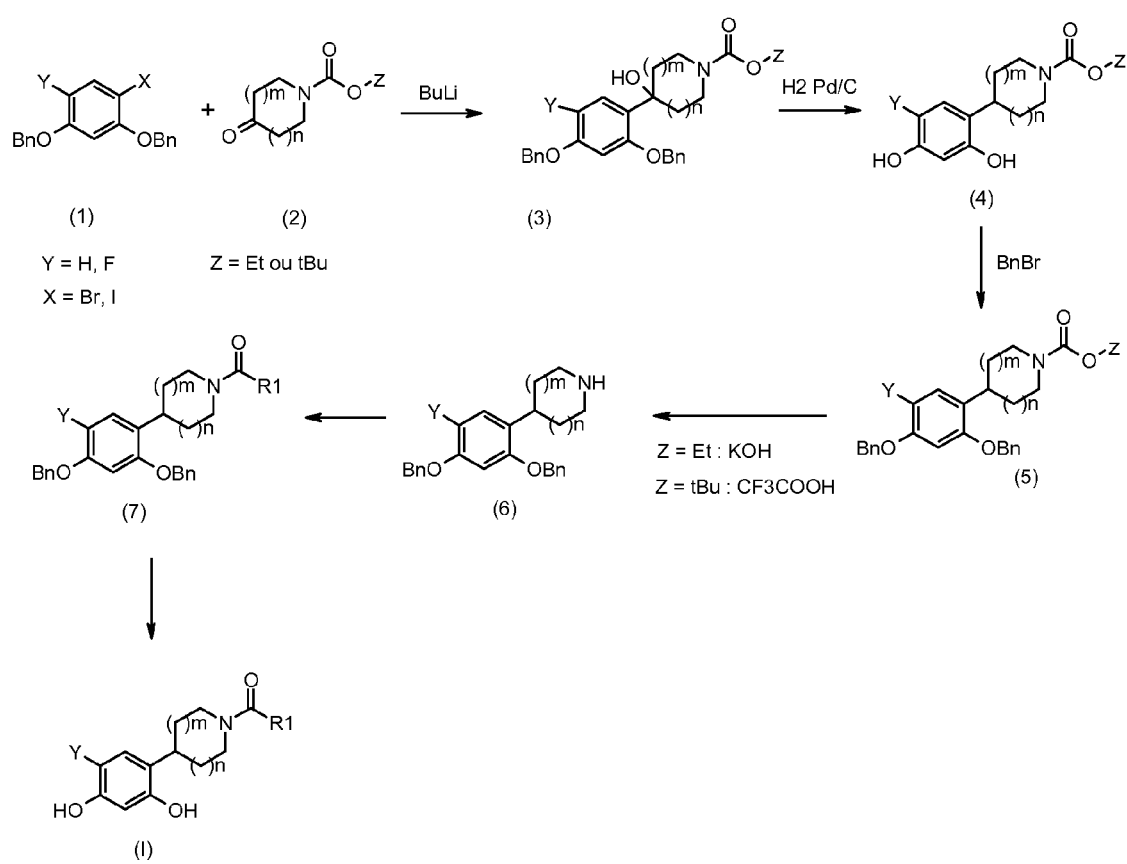

4-(AZACYCLOALKYL)BENZENE-1,3-DIOL COMPOUNDS AS TYROSINASE INHIBITORS, PROCESS FOR THE PREPARATION THEREOF AND USE THEREOF IN HUMAN MEDICINE AND IN COSMETICS

This application claims priority under 35 U.S.C. §119 of FR 0858207, filed Dec. 2, 2008, and U.S. Provisional Application Ser. No. 61/193,460, filed Dec. 2, 2008, and is the United States national phase of PCT/EP2009/066268, filed Dec. 2, 2009, and designating the United States (published in the English language on Jun. 10, 2010, as WO 2010/063774 A1; the title and abstract were also published in English), each hereby expressly incorporated by reference in its entirety and each assigned to the assignee hereof.

The invention relates to novel 4-(azacycloalkyl)benzene-1,3-diol compounds as industrial and useful products. It also relates to the process for the preparation thereof and to the use thereof, as tyrosinase inhibitors, in pharmaceutical or cosmetic compositions for use in the treatment or prevention of pigmentary disorders.

Skin pigmentation, in particular human skin pigmentation, is the result of melanin synthesis by dendritic cells, melanocytes. Melanocytes contain organelles called melanosomes which transfer melanin into the upper layers of keratinocytes which are then transported to the surface of the skin through differentiation of the epidermis (Gilchrest B A, Park H Y, Eller M S, Yaar M, Mechanisms of ultraviolet light-induced pigmentation. Photochem Photobiol 1996; 63: 1-10; Hearing V J, Tsukamoto K, Enzymatic control of pigmentation in mammals. FASEB J 1991; 5: 2902-2909).

Among the enzymes of melanogenesis, tyrosinase is a key enzyme which catalyses the first two steps of melanin synthesis. Homozygous mutations of tyrosinase cause oculocutaneous albinism type I characterized by a complete lack of melanin synthesis (Toyofuku K, Wada I, Spritz R A, Hearing V J, The molecular basis of oculocutaneous albinism type 1 (OCA1): sorting failure and degradation of mutant tyrosinases results in a lack of pigmentation. Biochem J 2001; 355: 259-269).

In order to treat pigmentation disorders resulting from an increase in melanin production, for which there is no treatment that meets all the expectations of patients and dermatologists, it is important to develop new therapeutic approaches.

Most of the skin-lightening compounds that are already known are phenols or hydroquinone derivatives. These compounds inhibit tyrosinase, but the majority of them are cytotoxic to melanocytes owing to the formation of quinones. There is a risk of this toxic effect causing a permanent depigmentation of the skin. The obtaining of compounds that can inhibit melanogenesis while at the same time being very weakly cytotoxic or devoid of toxicity to melanocytes is most particularly sought.

Among the compounds already described in the literature, patent application WO 99/15148 discloses the use of 4-cycloalkyl resorcinols as depigmenting agents.

Patent FR2704428 discloses the use of 4-halo-resorcinols as depigmenting agents.

Patent applications WO 2006/097224 and WO 2006/097223 disclose the use of 4-cycloalkylmethyl resorcinols as depigmenting agents.

Patent application WO 2005/085169 discloses the use of alkyl 3-(2,4-dihydroxyphenyl)propionate as a depigmenting agent.

Patent application WO 2004/017936 discloses the use of 3-(2,4-dihydroxyphenyl)acrylamide as a depigmenting agent.

Patent application WO 2004/052330 discloses the use of 4-[1,3]dithian-2-ylresorcinols as depigmenting agents.

More particularly, patent EP0341664 discloses the use of 4-alkyl resorcinols as depigmenting agents, among which 4-n-butyl resorcinol, also known as rucinol, is part of the composition of a depigmenting cream sold under the name Iklen®.

The applicant has now discovered, unexpectedly and surprisingly, that novel compounds of 4-(azacycloalkyl)benzene-1,3-diol structure have a very good tyrosinase enzyme-inhibiting activity and a very low cytotoxicity. Furthermore, these compounds have a tyrosinase enzyme-inhibiting activity that is greater than that of rucinol while at the same time being less cytotoxic with respect to melanocytes than rucinol.

These compounds find uses in human medicine, in particular in dermatology, and in the cosmetics field.

Thus, the present invention relates to the compounds of general formula (I) below:

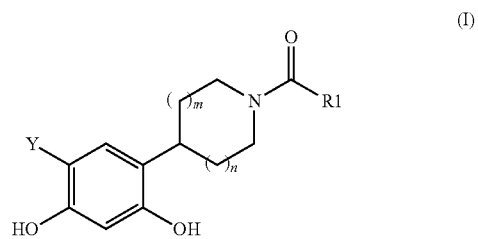

(I)

in which:

R1 represents:
- a $C_1$-$C_5$ alkyl radical,
- a $C_3$-$C_6$ cycloalkyl radical,
- an aryl radical,
- a substituted aryl radical,
- an aralkyl radical,
- a $C_1$-$C_5$ alkoxy radical,
- an amino radical corresponding to structure (a):

(a)

in which R2 represents:
- a hydrogen,
- a $C_1$-$C_5$ alkyl radical,
- a $C_3$-$C_6$ cycloalkyl radical,
- an aryl radical,
- a substituted aryl radical,
- a pyridyl radical,
- an aralkyl radical,
- a radical corresponding to structure (b):

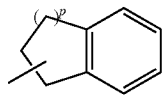
(b)

in which p can have the value 1 or 2,
a radical corresponding to structure (c):

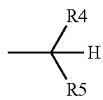
(c)

in which R4 represents:
a carboxymethyl —COOCH$_3$ or carboxyethyl —COOEt radical,
a C$_1$-C$_3$ alkyl radical,
a hydrogen,
and R5 represents:
a substituted or unsubstituted aryl radical,
a C$_3$-C$_6$ cycloalkyl radical,
a pyridyl,
and R3 represents:
a hydrogen,
a C$_1$-C$_5$ alkyl radical;
R1 may also represent a radical corresponding to formula (d):

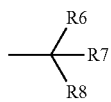
(d)

in which R6 represents:
a hydrogen,
a C$_1$-C$_5$ alkyl radical,
a C$_3$-C$_6$ cycloalkyl radical,
an aryl radical,
a substituted aryl radical,
a pyridyl radical,
an aralkyl radical,
R7 represents:
a hydrogen,
a C$_1$-C$_5$ alkyl radical,
and R8 represents:
a hydrogen,
a hydroxyl,
an amino radical,
a C$_1$-C$_3$ alkoxy radical;
Y represents a hydrogen or a fluorine, and
m and n can have the value 0, 1 or 2,
and also the salts of the compounds of formula (I), and the isomer and enantiomer forms thereof.

Among the salts of the compounds of general formula (I) with a pharmaceutically acceptable base, mention may preferably be made of the salts with an organic base or with an inorganic base.

The suitable inorganic bases are, for example, potassium hydroxide, sodium hydroxide or calcium hydroxide.

The suitable organic bases are, for example, morpholine, piperazine or lysine.

The compounds of general formula (I) may also exist in the form of hydrates or of solvates.

The solvents that are suitable for forming solvates are, for example, alcohols such as ethanol or isopropanol.

According to the present invention, the term "C$_1$-C$_5$ alkyl" denotes a linear or branched, saturated hydrocarbon-based chain containing from 1 to 5 carbon atoms.

According to the present invention, the term "C$_1$-C$_3$ alkyl" denotes a linear or branched, saturated hydrocarbon-based chain containing from 1 to 3 carbon atoms.

According to the present invention, the term "C$_3$-C$_6$ cycloalkyl" denotes a cyclic, saturated hydrocarbon-based chain containing from 3 to 6 carbon atoms.

According to the present invention, the term "aryl" denotes a phenyl or a naphthyl.

According to the present invention, the term "substituted aryl" denotes a phenyl or a naphthyl substituted with one or more groups of atoms chosen from an alkyl, an alkoxy, a fluorine and a trifluoromethyl.

According to the present invention, the term "aralkyl" denotes a C$_1$-C$_5$ alkyl radical as defined above and substituted with a substituted or unsubstituted aryl radical.

According to the present invention, the term "C$_1$-C$_5$ alkoxy" denotes an oxygen atom substituted with a linear or branched, saturated hydrocarbon-based chain containing from 1 to 5 carbon atoms.

According to the present invention, the term "C$_1$-C$_3$ alkoxy" denotes an oxygen atom substituted with a linear or branched, saturated hydrocarbon-based chain containing from 1 to 3 carbon atoms.

According to the present invention, the compounds of general formula (I) that are particularly preferred are those for which:
R1 represents an aralkyl radical or an amino radical corresponding to structure (a):

(a)

in which R2 represents:
a C$_1$-C$_5$ alkyl radical,
an aralkyl radical or
a radical corresponding to structure (d):

(d)

in which R4 represents:
a carboxymethyl —COOCH$_3$ or carboxyethyl —COOEt radical,
a C$_1$-C$_3$ alkyl radical, and R5 represents:
a substituted or unsubstituted aryl radical,
and R3 represents a hydrogen,
Y represents a hydrogen atom or a fluorine,
m=1 and n=1,
and also the salts of these compounds of general formula (I), and the isomer and enantiomer forms thereof.

Among the compounds of formula (I) which are part of the context of the present invention, mention may in particular be made of the following:

1: 3-(2,4-dihydroxyphenyl)azetidine-1-carboxylic acid tert-butyl ester
2: [3-(2,4-dihydroxyphenyl)azetidin-1-yl]phenyl-methanone
3: 3-(2,4-dihydroxyphenyl)azetidine-1-carboxylic acid pentylamide
4: 3-(2,4-dihydroxyphenyl)pyrrolidine-1-carboxylic acid tert-butyl ester
5: 3-(2,4-dihydroxyphenyl)pyrrolidine-1-carboxylic acid isobutyl ester
6: 3-(2,4-dihydroxyphenyl)pyrrolidine-1-carboxylic acid cyclohexylamide
7: 3-(2,4-dihydroxyphenyl)pyrrolidine-1-carboxylic acid phenylamide
8: 3-(2,4-dihydroxyphenyl)pyrrolidine-1-carboxylic acid (4-fluorophenyl)amide
9: 3-(2,4-dihydroxyphenyl)pyrrolidine-1-carboxylic acid (4-trifluoromethylphenyl)amide
10: 4-(2,4-dihydroxyphenyl)piperidine-1-carboxylic acid ethyl ester
11: [4-(2,4-dihydroxyphenyl)piperidin-1-yl]phenyl-methanone
12: 4-(2,4-dihydroxyphenyl)piperidine-1-carboxylic acid butylamide
13: 4-(2,4-dihydroxyphenyl)piperidine-1-carboxylic acid propylamide
14: 1-[4-(2,4-dihydroxyphenyl)piperidin-1-yl]butan-1-one
15: 1-[4-(2,4-dihydroxyphenyl)piperidin-1-yl]-2-methyl-propan-1-one
16: 4-(2,4-dihydroxyphenyl)piperidine-1-carboxylic acid phenylamide
17: 4-(2,4-dihydroxyphenyl)piperidine-1-carboxylic acid (4-fluorophenyl)amide
18: 4-(2,4-dihydroxyphenyl)piperidine-1-carboxylic acid p-tolylamide
19: 4-(2,4-dihydroxyphenyl)piperidine-1-carboxylic acid phenethylamide
20: 4-(2,4-dihydroxyphenyl)piperidine-1-carboxylic acid (3-fluorophenyl)amide
21: 4-(2,4-dihydroxyphenyl)piperidine-1-carboxylic acid ((R)-1-phenylethyl)amide
22: 4-(2,4-dihydroxyphenyl)piperidine-1-carboxylic acid methylphenylamide
23: 4-(2,4-dihydroxyphenyl)piperidine-1-carboxylic acid pyridin-2-ylamide
24: 4-(2,4-dihydroxyphenyl)piperidine-1-carboxylic acid ((S)-1-phenylethyl)amide
25: 4-(2,4-dihydroxyphenyl)piperidine-1-carboxylic acid ((S)-1-phenylpropyl)amide
26: (R)-2-amino-1-[4-(2,4-dihydroxyphenyl)piperidin-1-yl]-3-phenylpropan-1-one
27: 1-[4-(2,4-dihydroxyphenyl)piperidin-1-yl]-3-phenyl-propan-1-one
28: 4-(2,4-dihydroxyphenyl)piperidine-1-carboxylic acid 2-fluorobenzylamide
29: 4-(2,4-dihydroxyphenyl)piperidine-1-carboxylic acid 3-fluorobenzylamide
30: 4-(2,4-dihydroxyphenyl)piperidine-1-carboxylic acid 4-fluorobenzylamide
31: 4-(2,4-dihydroxyphenyl)piperidine-1-carboxylic acid benzylamide
32: 4-(2,4-dihydroxyphenyl)piperidine-1-carboxylic acid 2-methylbenzylamide
33: 4-(2,4-dihydroxyphenyl)piperidine-1-carboxylic acid 3-methylbenzylamide
34: 4-(2,4-dihydroxyphenyl)piperidine-1-carboxylic acid 4-methylbenzylamide
35: 4-(2,4-dihydroxyphenyl)piperidine-1-carboxylic acid 2-methoxybenzylamide
36: 4-(2,4-dihydroxyphenyl)piperidine-1-carboxylic acid 3-methoxybenzylamide
37: 4-(2,4-dihydroxyphenyl)piperidine-1-carboxylic acid 4-methoxybenzylamide
38: 4-(2,4-dihydroxyphenyl)piperidine-1-carboxylic acid ((S)-1-p-tolylethyl)amide
39: 4-(2,4-dihydroxyphenyl)piperidine-1-carboxylic acid [(S)-1-(4-fluorophenyl)ethyl]amide
40: 4-(2,4-dihydroxyphenyl)piperidine-1-carboxylic acid (S)-indan-1-ylamide
41: 4-(2,4-dihydroxyphenyl)piperidine-1-carboxylic acid ((S)-1-naphthalen-1-ylethyl)amide
42: 4-(2,4-dihydroxyphenyl)piperidine-1-carboxylic acid ((S)-1-naphthalen-2-ylethyl)amide
43: 4-(2,4-dihydroxyphenyl)piperidine-1-carboxylic acid [(S)-1-(4-methoxyphenyl)ethyl]amide
44: 4-(2,4-dihydroxyphenyl)piperidine-1-carboxylic acid [(S)-1-(3-methoxyphenyl)ethyl]amide
45: (S)-2-amino-1-[4-(2,4-dihydroxyphenyl)piperidin-1-yl]-3-phenylpropan-1-one
46: 4-(5-fluoro-2,4-dihydroxyphenyl)piperidine-1-carboxylic acid ((S)-1-phenylethyl)amide
47: (R)-1-[4-(2,4-dihydroxyphenyl)piperidin-1-yl]-2-hydroxy-2-phenylethanone
48: (S)-1-[4-(2,4-dihydroxyphenyl)piperidin-1-yl]-2-hydroxy-2-phenylethanone
49: (R)-1-[4-(2,4-dihydroxyphenyl)piperidin-1-yl]-2-hydroxy-3-phenylpropan-1-one
50: (S)-1-[4-(2,4-dihydroxyphenyl)piperidin-1-yl]-2-hydroxy-3-phenylpropan-1-one
51: (R)-2-amino-1-[4-(2,4-dihydroxyphenyl)piperidin-1-yl]-2-(4-fluorophenyl) ethanone
52: (R)-2-amino-1-[4-(2,4-dihydroxyphenyl)piperidin-1-yl]-2-phenylethanone
53: (S)-2-amino-1-[4-(2,4-dihydroxyphenyl)piperidin-1-yl]-2-phenylethanone
54: (R)-2-amino-1-[4-(2,4-dihydroxyphenyl)piperidin-1-yl]-2-(4-trifluoromethylphenyl)ethanone
55: 2-amino-1-[4-(2,4-dihydroxyphenyl)piperidin-1-yl]-2-phenylbutan-1-one
56: (S)-1-[4-(2,4-dihydroxyphenyl)piperidin-1-yl]-2-methoxy-2-phenylethanone
57: 4-(2,4-dihydroxyphenyl)piperidine-1-carboxylic acid ((S)-1-cyclohexylethyl)amide
58: 4-(2,4-dihydroxyphenyl)piperidine-1-carboxylic acid (1,2,3,4-tetrahydronaphthalen-1-yl)amide
59: (R)-{[4-(2,4-dihydroxyphenyl)piperidine-1-carbonyl]amino}phenylacetic acid methyl ester
60: 4-(2,4-dihydroxyphenyl)piperidine-1-carboxylic acid (pyridin-3-ylmethyl)amide
61: 4-(2,4-dihydroxyphenyl)piperidine-1-carboxylic acid (pyridin-4-ylmethyl)amide
62: 4-(5-fluoro-2,4-dihydroxyphenyl)piperidine-1-carboxylic acid benzylamide
63: 4-(5-fluoro-2,4-dihydroxyphenyl)piperidine-1-carboxylic acid butylamide
64: 4-(5-fluoro-2,4-dihydroxyphenyl)piperidine-1-carboxylic acid (3-fluorophenyl)amide
65: 4-(5-fluoro-2,4-dihydroxyphenyl)piperidine-1-carboxylic acid phenethylamide 66: (R)-{[4-(5-fluoro-2,4-dihydroxyphenyl)piperidine-1-carbonyl]amino}phenylacetic acid methyl ester
67: 4-(5-fluoro-2,4-dihydroxyphenyl)piperidine-1-carboxylic acid (S)-indan-1-ylamide
68: 4-(5-fluoro-2,4-dihydroxyphenyl)piperidine-1-carboxylic acid [(S)-1-(4-methoxyphenyl)ethyl]amide
69: 4-(5-fluoro-2,4-dihydroxyphenyl)piperidine-1-carboxylic acid ((S)-1-cyclohexylethyl)amide
70: (R)-1-[4-(5-fluoro-2,4-dihydroxyphenyl)piperidin-1-yl]-2-hydroxy-2-phenylethanone
71: (S)-1-[4-(5-fluoro-2,4-dihydroxyphenyl)piperidin-1-yl]-2-hydroxy-2-phenylethanone
72: (R)-2-amino-1-[4-(5-fluoro-2,4-dihydroxyphenyl)-piperidin-1-yl]-2-phenylethanone
73: (S)-2-amino-1-[4-(5-fluoro-2,4-dihydroxyphenyl)-piperidin-1-yl]-2-phenylethanone
74: (R)-1-[4-(5-fluoro-2,4-dihydroxyphenyl)piperidin-1-yl]-2-hydroxy-2-phenylpropan-1-one
75: (S)-1-[4-(5-fluoro-2,4-dihydroxyphenyl)piperidin-1-yl]-2-hydroxy-2-phenylpropan-1-one
76: (R)-1-[4-(2,4-dihydroxyphenyl)piperidin-1-yl]-2-hydroxy-2-phenylpropan-1-one
77: (S)-1-[4-(2,4-dihydroxyphenyl)piperidin-1-yl]-2-hydroxy-2-phenylpropan-1-one
78: (R)-{[4-(2,4-dihydroxyphenyl)piperidine-1-carbonyl]amino}-(4-fluorophenyl)acetic acid methyl ester
79: (S)-{[4-(2,4-dihydroxyphenyl)piperidine-1-carbonyl]amino}-(4-fluorophenyl)acetic acid methyl ester
80: (R)-1-[4-(2,4-dihydroxyphenyl)piperidin-1-yl]-2-hydroxy-2-methyl-3-phenylpropan-1-one
81: (S)-1-[4-(2,4-dihydroxyphenyl)piperidin-1-yl]-2-hydroxy-2-methyl-3-phenylpropan-1-one
82: 4-(5-fluoro-2,4-dihydroxyphenyl)piperidine-1-carboxylic acid (pyridin-3-ylmethyl)amide
83: 4-(5-fluoro-2,4-dihydroxyphenyl)piperidine-1-carboxylic acid (pyridin-4-ylmethyl)amide
84: (5-fluoro-2,4-dihydroxyphenyl)piperidine-1-carboxylic acid ((R)-1-phenylethyl)amide
85: (R)-1-[4-(2,4-dihydroxyphenyl)piperidin-1-yl]-2-hydroxy-2-phenylbutan-1-one
86: (S)-1-[4-(2,4-dihydroxyphenyl)piperidin-1-yl]-2-hydroxy-2-phenylbutan-1-one
87: (S)-1-[4-(2,4-dihydroxyphenyl)piperidin-1-yl]-2-(4-fluorophenyl)-2-hydroxyethanone
88: (R)-1-[4-(2,4-dihydroxyphenyl)piperidin-1-yl]-2-(4-fluorophenyl)-2-hydroxyethanone
89: (S)-1-[4-(2,4-dihydroxyphenyl)piperidin-1-yl]-2-hydroxy-2-(3-methoxyphenyl)ethanone
90: (R)-1-[4-(2,4-dihydroxyphenyl)piperidin-1-yl]-2-hydroxy-2-(3-methoxyphenyl)ethanone.
91: 4-(5-fluoro-2,4-dihydroxyphenyl)piperidine-1-carboxylic acid cyclohexylmethylamide
92: 4-(2,4-dihydroxyphenyl)piperidine-1-carboxylic acid cyclohexylmethylamide
93: 4-(2,4-dihydroxyphenyl)piperidine-1-carboxylic acid (2-ethylbutyl)amide
94: 4-(5-fluoro-2,4-dihydroxyphenyl)piperidine-1-carboxylic acid (2-ethylbutyl)amide
95: 4-(2,4-dihydroxyphenyl)piperidine-1-carboxylic acid cyclopentylmethylamide
96: 4-(5-fluoro-2,4-dihydroxyphenyl)piperidine-1-carboxylic acid cyclopentylmethylamide
97: 4-(2,4-dihydroxyphenyl)piperidine-1-carboxylic acid (6-methylpyridin-3-ylmethyl)amide
98: 4-(2,4-dihydroxyphenyl)piperidine-1-carboxylic acid (4-methylpyridin-3-ylmethyl)amide
99: 4-(2,4-dihydroxyphenyl)piperidine-1-carboxylic acid (5-methylpyridin-3-ylmethyl)amide
100: 4-(2,4-dihydroxyphenyl)piperidine-1-carboxylic acid (2-methylpyridin-3-ylmethyl)amide
101: 4-(2,4-dihydroxyphenyl)piperidine-1-carboxylic acid (2,6-dimethylpyridin-4-ylmethyl)amide
102: 4-(2,4-dihydroxyphenyl)piperidine-1-carboxylic acid (2-pyridin-2-ylethyl)amide
103: 4-(2,4-dihydroxyphenyl)piperidine-1-carboxylic acid (2-pyridin-3-ylethyl)amide
104: 4-(2,4-dihydroxyphenyl)piperidine-1-carboxylic acid (2-pyridin-4-ylethyl)amide The compounds of general formula (I) are prepared according to the general reaction scheme shown in FIG. 1.

The compounds 2,4-bis(benzyloxy)bromobenzene (X=Br; Y=H) or 1,5-bis(benzyloxy)-2-fluoro-4-iodobenzene (X=I; Y=F) (1), which are commercially available or prepared according to conventional synthesis methods (W. D. Langley, Org. Synth. I, 122 (1932)) (in the case of the fluoro compounds, Mottram, L. F.; Boonyarattanakalin, S.; Kovel, R. E.; Peterson, B. R. *Organic Letters* 2006, 8(4), 581-584) react in the presence of butyllithium, for example, with azacycloalkanones (2) which are commercially available or prepared according to conventional synthesis methods (W. D. Langley, Org. Synth. I, 122 (1932)) so as to give the corresponding benzyl alcohols of general formula (3) in which Y=H or F and Z=ethyl or tert-butyl (Annoura, H.; Nakanishi, K.; Uesugi, M.; Fukunaga, A.; Imajo, S.; Miyajima, A.; Tamura-Horikawa, Y.; Tamura, S.; *Bioorg Med Chem* 2002, 10 (2), 371-383).

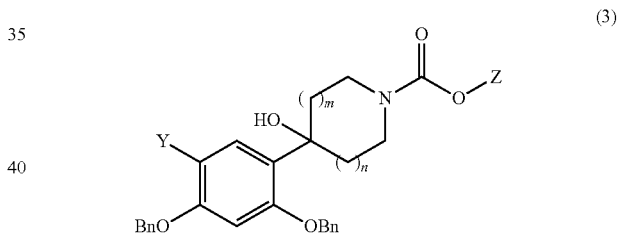

(3)

The compounds of general formula (4) are obtained by hydrogenation of the benzyl alcohols of general formula (3) in the presence of hydrogen and of a palladium-based catalyst such as palladium-on-charcoal, for example, in a solvent such as methanol (Merschaert, A.; Delhaye, L.; Kestemont, J.-P.; Brione, W.; Delbeke, P.; Mancuso, V.; Napora, F.; Diker, K.; Giraud, D.; Vanmarsenille, M.; *Tetrahedron Lett* 2003, 44 (24), 4531-4534).

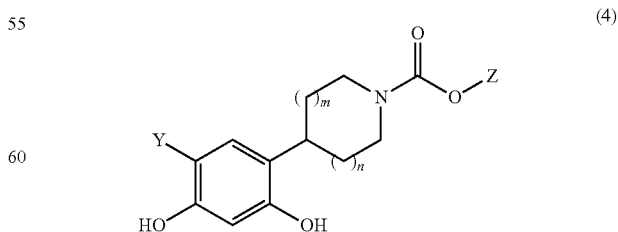

(4)

The compounds of general formula (4) may be benzylated using benzyl bromide and a base such as potassium carbonate, for example, in a solvent such as methyl ethyl ketone, for example, in order to give the compounds of general formula (5) (Bolek, D.; Guetschow, M.; *J Heterocycl Chem* 2005, 42 (7), 1399-1403).

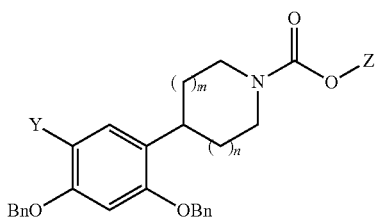

(5)

The compounds of general formula (5) are converted to amines of general formula (6) through the action of trifluoroacetic acid, for example, if Z=tert-butyl (Kasyan, A.; Wagner, C.; Maier, M. E.; *Tetrahedron* 1998, 54 (28), 8047-8054) or else through the action of an aqueous solution of potassium hydroxide, for example, if Z=ethyl (Morice, C.; Domostoj, M.; Briner, K.; Mann, A.; Suffert, J.; Wermuth, C.-G.; *Tetrahedron Lett* 2001, 42 (37), 6499-6502).

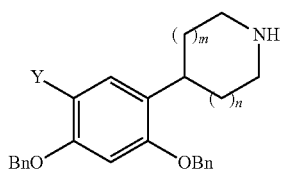

(6)

The compounds of general formula (6) are subsequently converted to compounds of general formula (7).

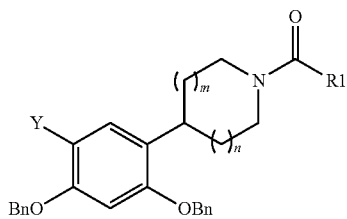

(7)

The compounds of general formula (7) may:
either be ureas: they are obtained by reacting the compounds of general formula (6) with isocyanates, for example (Ranise, A.; Schenone, S.; Bruno, O.; Bondavalli, F.; Filippelli, W.; Falcone, G.; Rivaldi, B.; *Farmaco* 2001, 56 (9), 647-657);
or be amides; they are obtained by reacting the compounds of general formula (6) with acyl chlorides, for example (Katritzky, A. R.; Singh, S. K.; Cai, C.; Bobrov, S.; *J Org Chem* 2006, 71(9), 3364-3374) or with acids (De Laszlo, S. E.; Allen, E. E.; Li, B.; Ondeyka, D.; Rivero, R.; Malkowitz, L.; Molineaux, C.; Siciliano, S. J.; Springer, M. S.; Greenlee, W. J.; Mantlo, N.; *Bioorg Med Chem Lett* 1997, 7 (2), 213-218);
or be carbamates: they are obtained by reacting the compounds of general formula (6) with chloroformates, for example (Brackeen, M. F.; Cowan, D. J.; Stafford, J. A.; Schoenen, F. J.; Veal, J. M.; Domanico, P. L.; Rose, D.;
Strickland, A. B.; Verghese, M.; Feldman, P. L.; *J Med Chem* 1995, 38 (24), 4848-4854).

The compounds of general formula (I) are, finally, obtained by hydrogenation of the compounds of general formula (7) in the presence of hydrogen and of a palladium-based catalyst such as palladium-on-charcoal, for example, in a solvent such as methanol, for example.

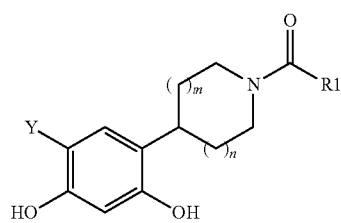

(I)

The invention is therefore directed towards the use of at least one compound of general formula (I) as defined above, as a medicament.

The invention is also directed towards the use, as a medicament, of at least one compound of general formula (I) as defined above, in which said compound has a tyrosinase-inhibiting activity.

The invention is also directed towards the use of at least one compound of general formula (I) as defined above, for the preparation of a pharmaceutical or cosmetic composition in which said compound has a tyrosinase-inhibiting activity.

Advantageously, the compounds of the present invention have an $IC_{50}$ value (dose which inhibits 50% of the enzymatic activity) with respect to tyrosinase of less than or equal to 10 μM, and more particularly less than or equal to 1 μM.

The invention also relates to a compound of general formula (I) for use thereof in the treatment and/or prevention of pigmentary disorders.

In fact, the compounds of general formula (I) according to the invention are particularly suitable for use related to the treatment or prevention of pigmentary disorders such as melasma, chloasma, lentigines, senile lentigo, irregular hyperpigmentations related to photoageing, freckles, post-inflammatory hyperpigmentations due to an abrasion, a burn, a scar, dermatosis, a contact allergy; naevi, genetically determined hyperpigmentations, hyperpigmentations of metabolic or drug-related origin, melanomas or any other hyperpigmentary lesion.

A subject of the present invention is also a pharmaceutical composition for use in particular in the treatment of the abovementioned conditions, and which is characterized in that it comprises, in a pharmaceutically acceptable carrier that is compatible with the method of administration selected for said composition, a compound of general formula (I) in one of its isomer and enantiomer forms, or a salt thereof with a pharmaceutically acceptable base.

The term "pharmaceutically acceptable carrier" is intended to mean a medium that is compatible with the skin, the mucous membranes and the skin appendages.

The composition according to the invention can be administered topically. Preferably, the pharmaceutical composition is packaged in a form suitable for topical application.

When used topically, the pharmaceutical composition according to the invention is more particularly for use in the treatment of the skin and the mucous membranes and may be in liquid, pasty or solid form, and more particularly in the form of ointments, creams, solutions or gels.

The compositions used for topical application have a concentration of compound according to the invention of generally between 0.001% and 10% by weight, preferably between 0.01% and 5% by weight, relative to the total weight of the composition.

The compounds of general formula (I) according to the invention also find a use in the cosmetics field, in particular in protecting against the harmful aspects of the sun, for preventing and/or combating photoinduced or chronological ageing of the skin and skin appendages.

A subject of the invention is therefore also a composition comprising, in a cosmetically acceptable carrier, at least one of the compounds of general formula (I). The term "cosmetically acceptable medium" is intended to mean a medium that is compatible with the skin, the mucous membranes and the skin appendages.

A subject of the invention is also the cosmetic use of a composition comprising at least one compound of general formula (I), for preventing and/or treating the signs of ageing and/or the skin.

A subject of the invention is also the cosmetic use of a composition comprising at least one compound of general formula (I), for body or hair hygiene.

The cosmetic composition according to the invention containing, in a cosmetically acceptable carrier, a compound of general formula (I), or one of its isomer and enantiomer forms or a salt thereof with a cosmetically acceptable base, may be in particular in the form of a cream, a milk, a gel, suspensions of microspheres or nanospheres or lipid or polymeric vesicles, impregnated pads, solutions, sprays, foams, sticks, soaps, washing bases or shampoos.

The concentration of compound of general formula (I) in the cosmetic composition is preferably between 0.001% and 10% by weight, relative to the total weight of the composition.

The pharmaceutical and cosmetic compositions as described above may also contain inert additives, or even pharmacodynamically active additives as regards the pharmaceutical compositions, or combinations of these additives, and in particular:
  wetting agents;
  flavour enhancers;
  preservatives, such as para-hydroxybenzoic acid esters;
  stabilizers;
  moisture regulators;
  pH regulators;
  osmotic pressure modifiers;
  emulsifiers;
  UV-A and UV-B screening agents;
  antioxidants, such as α-tocopherol, butylated hydroxyanisole or butylated hydroxytoluene, superoxide dismutase, ubiquinol; sodium metabisulphite;
  emollients;
  moisturizing agents, such as glycerol, PEG 400, thiamorpholinone and its derivatives, or urea;
  antiseborrhoeic or antiacne agents, such as S-carboxymethylcysteine, S-benzylcysteamine, salts thereof or derivatives thereof, or benzoyl peroxide.

Of course, those skilled in the art will take care to select the optional compound(s) to be added to these compositions in such a way that the advantageous properties intrinsically associated with the present invention are not, or not substantially, impaired by the envisaged addition.

Several examples of the preparation of compounds of general formula (I) according to the invention, results for biological activity of these compounds and also various formulations based on such compounds will now be given by way of illustration and without any limiting nature.

EXAMPLE 1

3-(2,4-Dihydroxyphenyl)azetidine-1-carboxylic acid tert-butyl ester a) 2,4-Bis(benzyloxy)-1-bromobenzene 106.6 g (0.771 mol, 3 eq) of potassium carbonate (325 mesh) are added to a solution of 50.1 g (0.257 mol, 1 eq) of 4-bromoresorcinol at 97% in 500 ml of acetone. The reaction medium is cooled to 5-10° C. and 75 ml (0.630 mol, 2.45 eq) of benzyl bromide are added dropwise. The reaction medium is stirred at ambient temperature overnight and is then heated at 50° C. for 2 hours. The solvent is evaporated off and the residue is then taken up with a water/ethyl acetate mixture. The aqueous phase is extracted with ethyl acetate, and the organic phases are combined, washed with a saturated solution of sodium chloride, dried over magnesium sulphate, filtered and evaporated. The residue (114.34 g) is chromatographed on silica gel (600 g), elution being carried out with 90/10 heptane/dichloromethane.

94.4 g of 2,4-bis(benzyloxy)-1-bromobenzene are obtained in the form of white crystals. Yield=99%.

b) 3-(2,4-Bis(benzyloxy)phenyl)-3-hydroxyazetidine-1-carboxylic acid tert-butyl ester In a 100 ml three-necked flask, 5 g of 2,4-bis(benzyloxy)-1-bromobenzene are dissolved in 60 ml of tetrahydrofuran. The mixture is cooled to −70° C. and then 11.4 ml of 2.5M n-butyllithium in hexane are added. The reaction medium is stirred at −70° C. for 1 hour, and then 2.8 g of 1-Boc-azetidine-3-one dissolved in 4 ml of THF are added dropwise. The reaction medium is stirred at −70° C. for 2 hours and then left at ambient temperature overnight. The reaction medium is poured into 40 ml of a 2M solution of hydrochloric acid and then extracted with 100 ml of ethyl acetate. The organic phases are combined, washed with 50 ml of water and then dried over magnesium sulphate and evaporated. The residue is chromatographed on silica gel (AnaLogix SF40-80 g column), elution being carried out with 80/20 heptane/ethyl acetate. 2.2 g of 3-(2,4-bis(benzyloxy)phenyl)-3-hydroxyazetidine-1-carboxylic acid tert-butyl ester are obtained. Yield: 37%.

c) 3-(2,4-Dihydroxyphenyl)azetidine-1-carboxylic acid tert-butyl ester 1 g of 3-(2,4-bis(benzyloxy)phenyl)-3-hydroxyazetidine-1-carboxylic acid tert-butyl ester are dissolved in a mixture of 20 ml of ethyl acetate/10 ml of methanol, and then 0.2 g of palladium-on-charcoal at 10% is added. The reaction mixture is stirred for 24 hours under a hydrogen atmosphere. The reaction mixture is filtered and then the residue is chromatographed on silica gel (7/3 heptane/ethyl acetate). 0.16 g of 3-(2,4-dihydroxyphenyl)azetidine-1-carboxylic acid tert-butyl ester is obtained. Yield=28%.

$^1$H NMR (DMSO, 400 MHz): 1.38 (s, 9H); 3.72 (m, 1H); 3.85 (bm, 2H); 4.07 (bm, 2H); 6.17 (dd, J=8.4 & 2.4 Hz, 1H); 6.27 (d, J=2.4 Hz, 1H); 6.92 (d, J=8.4 Hz, 1H); 9.12 (s, 1H); 9.32 (s, 1H).

$^{13}$C NMR (DMSO, 100 MHz): 28.1, 55, 102.4, 105.9, 117.9, 127.6, 155.8, 156.0, 157.0.

EXAMPLE 2

[3-(2,4-Dihydroxyphenyl)azetidin-1-yl]phenyl-methanone a) 3-(2,4-Bis(benzyloxy)phenyl)azetidine-1-carboxylic acid tert-butyl ester In a 25 ml round-bottomed flask, 1.35 g of potassium carbonate are added in small portions to a solution of 0.86 g of 3-(2,4-dihydroxyphenyl)azetidine-1-carboxylic acid tert-butyl ester (Example 1) in 9 ml of methyl ethyl ketone.

0.93 ml of benzyl bromide are added dropwise and the reaction mixture is then stirred for 2 hours at reflux. The reaction mixture is filtered and the residue is then chromatographed on silica gel (70/30 heptane/ethyl acetate).

1.1 g of 3-(2,4-bis(benzyloxy)phenyl)azetidine-1-carboxylic acid tert-butyl ester are obtained. Yield=76%.

b) 3-(2,4-Bis(benzyloxy)phenyl)azetidine trifluoroacetate

In a 25 ml round-bottomed flask, 1 g of 3-(2,4-bis(benzyloxy)phenyl)azetidine-1-carboxylic acid tert-butyl ester is dissolved in 10 ml of dichloromethane and then 2.5 ml of trifluoroacetic acid are added. The reaction mixture is stirred for 2 hours. The solvents are evaporated off and the residue is then taken up in isopropyl ether. 0.92 g of 3-(2,4-bis(benzyloxy)phenyl)azetidine trifluoroacetate is obtained. Yield=90%.

c) [3-(2,4-Bis(benzyloxy)phenyl)azetidin-1-yl]phenylmethanone

In a 10 ml round-bottomed flask, 0.25 g of 3-(2,4-bis(benzyloxy)phenyl)azetidine trifluoroacetate in 5 ml of tetrahydrofuran is dissolved in the presence of 0.1 ml of N,N-diisopropylethylamine. 0.07 ml of benzoyl chloride is added and the mixture is then stirred for 24 hours at ambient temperature. The reaction mixture is extracted with ethyl acetate and the organic phases are then combined and dried over magnesium sulphate. The residue is chromatographed on silica gel (9/1 heptane/ethyl acetate). 0.2 g of [3-(2,4-bis(benzyloxy)phenyl)azetidin-1-yl]phenylmethanone is obtained. Yield=82%.

d) [3-(2,4-Dihydroxyphenyl)azetidin-1-yl]phenyl-methanone

In a 10 ml round-bottomed flask, 0.2 g of [3-(2,4-bis(benzyloxy)phenyl)azetidin-1-yl]phenylmethanone is dissolved in 6 ml of methanol in the presence of 0.1 g of palladium-on-charcoal at 10%. The reaction mixture is stirred for 18 hours under a hydrogen atmosphere. The reaction mixture is filtered and the residue is then chromatographed on silica gel (1/1 heptane/ethyl acetate). 0.08 g of [3-(2,4-dihydroxyphenyl)azetidin-1-yl]phenylmethanone is obtained. Yield=67%.

$^1$H NMR (DMSO, 400 MHz): 3.86 (m, 1H); 4.04 (m, 1H); 4.29 (m, 2H); 4.58 (t, J=8.6 Hz, 1H); 6.19 (dd, J=8.4 & 2.4 Hz, 1H); 6.28 (d, J=2.4 Hz, 1H); 6.98 (d, J=8.4 Hz, 1H); 7.47 (m, 3H); 7.63 (d, J=8 Hz, 2H) 9.14 (s, 1H); 9.37 (s, 1H).

$^{13}$C NMR (DMSO, 100 MHz): 29.3, 54.2, 58.7, 102.4, 105.9, 117.8, 127.7, 127.8, 128.3, 130.7, 133.3, 156.0, 157.0, 168.9.

EXAMPLE 3

3-(2,4-Dihydroxyphenyl)azetidine-1-carboxylic acid pentylamide a) 3-(2,4-Bis(benzyloxy)phenyl)azetidine-1-carboxylic acid pentylamide In a 10 ml round-bottomed flask, 0.15 g of 3-(2,4-bis(benzyloxy)phenyl)azetidine trifluoroacetate is dissolved in 3 ml of tetrahydrofuran in the presence of 0.1 ml of N,N-diisopropylethylamine. 0.04 ml of pentyl isocyanate is added and the reaction mixture is then stirred for 20 minutes at ambient temperature. The reaction mixture is extracted with ethyl acetate and the organic phases are then combined and dried over magnesium sulphate. The residue is chromatographed on silica gel (9/1 heptane/ethyl acetate). 0.1 g of 3-(2,4-bis(benzyloxy)phenyl)azetidine-1-carboxylic acid pentylamide is obtained. Yield=67%.

b) 3-(2,4-Dihydroxyphenyl)azetidine-1-carboxylic acid pentylamide

In a 10 ml round-bottomed flask, 0.2 g of 3-(2,4-bis(benzyloxy)phenyl)azetidine-1-carboxylic acid pentylamide is dissolved in 6 ml of methanol in the presence of 0.1 g of palladium-on-charcoal at 10%. The reaction mixture is stirred for 6 hours under a hydrogen atmosphere. The reaction mixture is filtered and the residue is then chromatographed on silica gel (95/5 dichloromethane/methanol).

0.02 g of 3-(2,4-dihydroxyphenyl)azetidine-1-carboxylic acid pentylamide is obtained. Yield=33%.

$^1$H NMR (DMSO, 400 MHz): 0.85 (t, J=7 Hz, 3H); 1.22 (m, 4H); 1.34 (m, 2H); 2.94 (bm, 2H); 3.59 (bm, 1H); 3.73 (bm, 2H); 4.02 (bm, 2H); 6.17 (m, 3H); 6.26 (d, J=2.4 Hz, 1H); 6.91 (d, J=8.4 Hz, 1H); 9.1 (bs, 1H); 9.27 (s, 1H).

$^{13}$C NMR (DMSO, 100 MHz): 13.9, 21.9, 27.6, 28.5, 29.6, 55.0, 102.3, 106.0, 118.5, 127.3, 155.8, 156.8, 159.9.

EXAMPLE 4

3-(2,4-Dihydroxyphenyl)pyrrolidine-1-carboxylic acid tert-butyl ester a) 3-Oxo-pyrrolidine-1-carboxylic acid tert-butyl ester In a 1 l three-necked flask, 10 g of N-Boc-3-hydroxypyrrolidine are dissolved in 350 ml of dimethyl sulphoxide in the presence of 52.3 ml of triethylamine. 28 g of pyridine-sulphur trioxide complex dissolved in 350 ml of dimethyl sulphoxide are added dropwise to the above solution. The reaction mixture is stirred for 4 hours at ambient temperature. The reaction medium is acidified to pH 4.5-5 with a 1M solution of hydrochloric acid and the reaction mixture is then extracted with ethyl acetate. The organic phases are combined and then dried over anhydrous sodium sulphate. The residue is filtered through silica gel (1/1 heptane/ethyl acetate). 5.7 g of 3-oxo-pyrrolidine-1-carboxylic acid tert-butyl ester are obtained. Yield: 58%.

b) 3-(2,4-Dihydroxyphenyl)pyrrolidine-1-carboxylic acid tert-butyl ester

In a manner analogous to Examples 1b and 1c, but using 3-oxo-pyrrolidine-1-carboxylic acid tert-butyl ester, 3-(2,4-dihydroxyphenyl)pyrrolidine-1-carboxylic acid tert-butyl ester is obtained.

¹H NMR (DMSO, 400 MHz): 1.40 (s, 9H); 1.89 (m, 2H); 3.04 (t, J=9.5 Hz, 1H); 3.23 (m, 1H); 3.36 (m, 2H); 3.57 (dd, J=7.6 & 10 Hz, 1H); 6.14 (dd, J=8.4 & 2.4 Hz, 1H); 6.28 (d, J=2.4 Hz, 1H); 6.82 (m, 1H); 9.06 (s, 1H); 9.27 (s, 1H).

¹³C NMR (DMSO, 100 MHz): 28.1, 29.9 & 30.8, 36.2 & 37.2, 45.2 & 45.4, 50.7 & 51.1, 78.0, 102.5, 106.0, 127.1, 153.5, 155.5, 156.7.

EXAMPLE 5

3-(2,4-Dihydroxyphenyl)pyrrolidine-1-carboxylic acid isobutyl ester a) 3-(2,4-Bis(benzyloxy)phenyl)pyrrolidinium trifluoroacetate In a 50 ml round-bottomed flask, 1 g of 3-(2,4-bis(benzyloxy)phenyl)pyrrolidine-1-carboxylic acid tert-butyl ester (Example 4) are dissolved in 16 ml of dichloromethane and then 4 ml of trifluoroacetic acid are added. The reaction mixture is stirred for 1 hour. The solvents are evaporated off and the residue is then taken up in isopropyl ether. 1.26 g of 3-(2,4-bis(benzyloxy)phenyl)pyrrolidinium trifluoroacetate are obtained. Yield=76%.

b) 3-(2,4-Bis(benzyloxy)phenyl)pyrrolidine-1-carboxylic acid isobutyl ester

In a 10 ml round-bottomed flask, 0.25 g of 3-(2,4-bis(benzyloxy)phenyl)pyrrolidinium trifluoroacetate is dissolved in 5 ml of tetrahydrofuran in the presence of 0.25 ml of N,N-diisopropylethylamine. 0.108 g of isobutyl chloroformate is added and the reaction mixture is stirred for 30 minutes at ambient temperature. The reaction mixture is extracted with ethyl acetate and the organic phases are then combined and dried over magnesium sulphate. The residue is chromatographed on silica gel (8/2 heptane/ethyl acetate). 0.22 g of 3-(2,4-bis(benzyloxy)phenyl)pyrrolidine-1-carboxylic acid isobutyl ester is obtained. Yield=66%.

c) 3-(2,4-Dihydroxyphenyl)pyrrolidine-1-carboxylic acid isobutyl ester

In a 25 ml round-bottomed flask, 0.22 g of 3-(2,4-bis(benzyloxy)phenyl)pyrrolidine-1-carboxylic acid isobutyl ester is dissolved in 6 ml of methanol in the presence of 0.1 g of palladium-on-charcoal at 10%. The reaction mixture is stirred for 18 hours under a hydrogen atmosphere. The reaction mixture is filtered and the residue is then chromatographed on silica gel (1/1 heptane/ethyl acetate).

0.1 g of 3-(2,4-dihydroxyphenyl)pyrrolidine-1-carboxylic acid isobutyl ester is obtained. Yield=75%.

¹H NMR (DMSO, 400 MHz): 0.88 (t, J=7 Hz, 6H); 1.80-2.07 (m, 3H); 3.10 (q, J=9 Hz, 1H); 3.23-3.48 (m, 3H); 3.63 (m, 1H); 3.75 (m, 2H); 6.14 (dd, J=8.4 & 2.4 Hz, 1H); 6.28 (d, J=2.4 Hz, 1H); 6.82 (m, 1H); 9.07 (s, 1H); 9.29 (s, 1H).

¹³C NMR (DMSO, 100 MHz): 18.9, 27.6, 30.0 & 30.8, 36.4 & 37.3, 45.0 & 45.5, 50.6 & 51.0, 70.1, 102.5, 106.0, 117.5, 127.0, 154.1, 155.9, 156.7.

EXAMPLE 6

3-(2,4-Dihydroxyphenyl)pyrrolidine-1-carboxylic acid cyclohexylamide a) 3-(2,4-Bis(benzyloxy)phenyl)pyrrolidine-1-carboxylic acid cyclohexylamide In a 10 ml round-bottomed flask, 0.25 g of 3-(2,4-bis(benzyloxy)phenyl)pyrrolidinium trifluoroacetate is dissolved in 5 ml of tetrahydrofuran in the presence of 0.25 ml of N,N-diisopropylethylamine. 0.1 g of cyclohexyl isocyanate is added and the reaction mixture is stirred for 30 minutes at ambient temperature. The reaction mixture is extracted with ethyl acetate and the organic phases are then combined and dried over magnesium sulphate. The residue is chromatographed on silica gel (7/3 heptane/ethyl acetate). 0.23 g of 3-(2,4-bis(benzyloxy)phenyl)pyrrolidine-1-carboxylic acid cyclohexylamide is obtained. Yield=66%.

b) 3-(2,4-Dihydroxyphenyl)pyrrolidine-1-carboxylic acid cyclohexylamide

In a 25 ml round-bottomed flask, 0.23 g of 3-(2,4-bis(benzyloxy)phenyl)pyrrolidine-1-carboxylic acid cyclohexylamide is dissolved in 4 ml of methanol in the presence of 3 ml of ethyl acetate and of 0.1 g of palladium-on-charcoal at 10%. The reaction mixture is stirred for 18 hours under a hydrogen atmosphere. The reaction mixture is filtered and the residue is then chromatographed on silica gel (7/3 heptane/ethyl acetate).

0.095 g of 3-(2,4-dihydroxyphenyl)pyrrolidine-1-carboxylic acid cyclohexylamide is obtained. Yield=100%.

¹H NMR (DMSO, 400 MHz): 1.17 (m, 4H); 1.55 (m, 1H); 1.60 (m, 4H); 1.86 (m, 1H); 1.99 (m, 1H); 3.03 (t, J=9.2 Hz, 1H); 3.21 (q, J=9.2 Hz, 1H); 3.38 (m, 3H); 3.56 (t, J=8 Hz, 1H); 5.67 (d, J=7.9 Hz, 1H); 6.14 (dd, J=8.4 & 2.4 Hz, 1H); 6.28 (d, J=2.4 Hz, 1H); 6.85 (d, J=8.2 Hz, 1H); 9.04 (s, 1H); 9.25 (s, 1H).

¹³C NMR (DMSO, 100 MHz): 25.1, 25.3, 30.6, 33.3, 36.9, 45.0, 48.7, 50.7, 102.4, 105.9, 118.0, 127.0, 155.8, 155.9, 156.6.

EXAMPLE 7

3-(2,4-Dihydroxyphenyl)pyrrolidine-1-carboxylic acid phenylamide

In a manner analogous to Example 6, but using phenyl isocyanate, 3-(2,4-dihydroxyphenyl)pyrrolidine-1-carboxylic acid phenylamide is obtained.

¹H NMR (DMSO, 400 MHz): 1.94-2.09 (m, 2H); 3.23 (t, J=9.4 Hz, 1H); 3.37 (m, 1H); 3.48 (m, 1H); 3.54 (m, 1H); 3.76 (dd, J=7.7 & 9.5 Hz, 1H); 6.17 (dd, J=8.4 & 2.4 Hz, 1H); 6.30 (d, J=2.4 Hz, 1H); 6.89 (m, 1H); 7.21 (t, J=7.6 Hz, 2H); 7.51 (d, J=7.6 Hz, 2H); 9.08 (s, 1H); 9.31 (s, 1H).

¹³C NMR (DMSO, 100 MHz): 30.5, 37.0, 45.4, 51.0, 102.4, 106.0, 117.7, 119.3, 121.4, 127.2, 128.2, 140.6, 153.8, 156.0, 156.7.

EXAMPLE 8

3-(2,4-Dihydroxyphenyl)pyrrolidine-1-carboxylic acid (4-fluorophenyl)amide

In a manner analogous to Example 6, but using 4-fluorophenyl isocyanate, 3-(2,4-dihydroxyphenyl)pyrrolidine-1-carboxylic acid (4-fluorophenyl)amide is obtained.

¹H NMR (DMSO, 400 MHz): 1.93-2.08 (m, 2H); 3.24 (t, J=9.4 Hz, 1H); 3.37 (m, 1H); 3.44 (m, 1H); 3.53 (m, 1H); 3.76 (dd, J=7.7 & 9.5 Hz, 1H); 6.17 (dd, J=8.4 & 2.4 Hz, 1H); 6.30 (d, J=2.4 Hz, 1H); 6.91 (d, J=8.3 Hz, 1H); 7.05 (t, J=8.8 Hz, 2H); 7.51 (m, 2H); 8.15 (s, 1H); 9.08 (s, 1H); 9.31 (s, 1H).

¹³C NMR (DMSO, 100 MHz): 30.5, 37.0, 45.4, 51.0, 102.5, 106.0, 114.7, 117.7, 121.0, 127.1, 137.0, 155.9, 156.7, 158.3.

EXAMPLE 9

3-(2,4-Dihydroxyphenyl)pyrrolidine-1-carboxylic acid (4-trifluoromethylphenyl)amide In a manner analogous to Example 6, but using 4-trifluoromethylphenyl isocyanate, 3-(2,4-dihydroxyphenyl)pyrrolidine-1-carboxylic acid (4-trifluoromethylphenyl)amide is obtained.

$^1$H NMR (DMSO, 400 MHz): 1.95-2.08 (m, 2H); 3.26 (t, J=9.4 Hz, 1H); 3.37 (m, 1H); 3.44 (m, 1H); 3.57 (m, 1H); 3.77 (dd, J=7.7 & 9.5 Hz, 1H); 6.17 (dd, J=8.4 & 2.4 Hz, 1H); 6.30 (d, J=2.4 Hz, 1H); 6.90 (d, J=8.3 Hz, 1H); 7.56 (d, J=8.7 Hz, 1H); 7.76 (d, J=8.7 Hz, 2H); 8.52 (s, 1H); 9.08 (s, 1H); 9.33 (s, 1H).

$^{13}$C NMR (DMSO, 100 MHz): 30.4, 37.0, 45.5, 51.0, 102.5, 106.0, 117.5, 118.6, 121.1 (q), 124.6 (q), 125.4, 127.2, 153.38, 156.0, 156.7.

EXAMPLE 10

4-(2,4-Dihydroxyphenyl)piperidine-1-carboxylic acid ethyl ester a) 4-(2,4-Bis(benzyloxy)phenyl)-4-hydroxypiperidine-1-carboxylic acid ethyl ester In a 500 ml three-necked flask, 20 g of 2,4-bis(benzyloxy)-1-bromobenzene are dissolved in 240 ml of tetrahydrofuran. The mixture is cooled to −70° C. and then 26 ml of 2.5M n-butyllithium in hexane are added. The reaction medium is stirred at −70° C. for 1 hour, and then 11.1 g of 4-oxopiperidine-1-carboxylic acid ethyl ester are added dropwise. The reaction medium is stirred at −70° C. for 2 hours and then left at ambient temperature overnight. The reaction medium is poured into 100 ml of a 2M solution of hydrochloric acid and then extracted with 400 ml of ethyl acetate. The organic phases are combined, washed with 150 ml of water and then dried over magnesium sulphate and evaporated.

The residue is crystallized with a dichloromethane/heptane mixture. 16 g of 4-(2,4-bis(benzyloxy)phenyl)-4-hydroxypiperidine-1-carboxylic acid ethyl ester are obtained. Yield: 62%.

b) 4-(2,4-Dihydroxyphenyl)piperidine-1-carboxylic acid ethyl ester 1 g of 4-(2,4-bis(benzyloxy)phenyl)-4-hydroxypiperidine-1-carboxylic acid ethyl ester is dissolved in a mixture of 50 ml of methanol, and then 0.5 g of palladium-on-charcoal at 10% is added. The reaction mixture is stirred for 2 hours under a hydrogen atmosphere. The reaction mixture is filtered and the residue is then crystallized with dichloromethane. 0.5 g of 4-(2,4-dihydroxyphenyl)piperidine-1-carboxylic acid ethyl ester is obtained. Yield=86%.

$^1$H NMR (DMSO, 400 MHz): 1.17 (t, J=7 Hz, 3H); 1.38 (m, 2H); 1.64 (m, 2H); 2.84 (m, 3H) 4.01 (m, 4H); 6.12 (dd, J=8.4 & 2.4 Hz, 1H); 6.25 (d, J=2.4 Hz, 1H); 6.79 (d, J=8.3 Hz, 1H); 8.96 (s, 1H); 9.14 (s, 1H).

$^{13}$C NMR (DMSO, 100 MHz): 14.6, 31.6, 34.6, 44.2, 60.5, 102.3, 106.0, 122.1, 126.7, 154.6, 155.2, 156.2.

EXAMPLE 11

[4-(2,4-Dihydroxyphenyl)piperidin-1-yl]phenylmethanone a) 4-(2,4-Bis(benzyloxy)phenyl)piperidine-1-carboxylic acid ethyl ester

In a 100 ml round-bottomed flask, 9.7 g of potassium carbonate are added in small portions to a solution of 6.2 g of 4-(2,4-dihydroxyphenyl)piperidine-1-carboxylic acid ethyl ester (Example 10) in 62 ml of methyl ethyl ketone.

6.7 ml of benzyl bromide are added dropwise and the reaction mixture is then stirred for 2 hours at reflux. The reaction mixture is filtered and the residue is then chromatographed on silica gel (80/20 heptane/ethyl acetate).

9.8 g of 4-(2,4-bis(benzyloxy)phenyl)piperidine-1-carboxylic acid ethyl ester are obtained. Yield=92%.

b) 4-(2,4-Bis(benzyloxy)phenyl)piperidine

In a 500 ml three-necked flask, 9 g of 4-(2,4-bis(benzyloxy)phenyl)piperidine-1-carboxylic acid ethyl ester are dissolved in 180 ml of ethanol, and then 40 ml of a 5M solution of sodium hydroxide are added. The reaction mixture is brought to reflux for 48 hours. The reaction mixture is poured into 400 ml of water. The solid is filtered off and then chromatographed on silica gel (98/2 dichloromethane/methanol). 3.8 g of 4-(2,4-bis(benzyloxy)phenyl)piperidine are obtained.

c) [4-(2,4-Bis(benzyloxy)phenyl)piperidin-1-yl]phenylmethanone

In a 25 ml round-bottomed flask, 0.5 g of 4-(2,4-bis(benzyloxy)phenyl)piperidine in 10 ml of tetrahydrofuran is dissolved in the presence of 0.26 ml of N,N-diisopropylethylamine. 0.17 ml of benzoyl chloride is added and the mixture is then stirred for 24 hours at ambient temperature. The reaction mixture is extracted with ethyl acetate and then the organic phases are combined and dried over magnesium sulphate. The residue is chromatographed on silica gel (8/2 heptane/ethyl acetate). 0.5 g of [4-(2,4-bis(benzyloxy)phenyl)piperidin-1-yl]phenylmethanone is obtained. Yield=80%.

d) [4-(2,4-Dihydroxyphenyl)piperidin-1-yl]phenylmethanone

In a 25 ml round-bottomed flask, 0.5 g of [4-(2,4-bis(benzyloxy)phenyl)piperidin-1-yl]phenylmethanone is dissolved in 15 ml of methanol in the presence of 0.2 g of palladium-on-charcoal at 10%. The reaction mixture is stirred for 48 hours under a hydrogen atmosphere. The reaction mixture is filtered and the residue is then chromatographed on silica gel (1/1 heptane/ethyl acetate).

0.3 g of [4-(2,4-dihydroxyphenyl)piperidin-1-yl]phenylmethanone is obtained. Yield=96%.

$^1$H NMR (DMSO, 400 MHz): 1.50 (bm, 2H); 1.59 (bm, 1H); 1.75, (bm, 1H); 2.79 (bm, 1H); 2.97 (m, 1H); 3.11 (bm, 1H); 3.62 (bm, 1H); 4.59 (bm, 1H); 6.14 (dd, J=8.4 & 2.4 Hz, 1H); 6.27 (d, J=2.4 Hz, 1H); 6.85 (d, J=8.3 Hz, 1H); 7.41 (m, 5H); 8.98 (s, 1H), 9.17 (s, 1H).

$^{13}$C NMR (DMSO, 100 MHz): 31.7, 34.6, 47.9, 102.4, 106.0, 122.0, 126.6, 126.9, 128.3, 129.2, 136.6, 139.6, 155.1, 156.1, 168.8, 170.3.

EXAMPLE 12

4-(2,4-Dihydroxyphenyl)piperidine-1-carboxylic acid butylamide a) 4-(2,4-Bis(benzyloxy)phenyl)piperidine-1-carboxylic acid butylamide

In a 10 ml round-bottomed flask, 0.25 g of 4-(2,4-bis(benzyloxy)phenyl)piperidine is dissolved in 5 ml of tetrahydrofuran in the presence of 0.23 ml of N,N-diisopropylethylamine. 0.08 ml of butyl isocyanate is added and the reaction mixture is then stirred for 20 minutes at ambient temperature. The reaction mixture is extracted with ethyl acetate, and then the organic phases are combined and dried over magnesium sulphate. The residue is chromatographed on silica gel (8/2 heptane/ethyl acetate). 0.25 g of 4-(2,4-bis(benzyloxy)phenyl)piperidine-1-carboxylic acid butylamide is obtained. Yield=78%.

b) 4-(2,4-Dihydroxyphenyl)piperidine-1-carboxylic acid butylamide

In a 25 ml round-bottomed flask, 0.25 g of 4-(2,4-bis(benzyloxy)phenyl)piperidine-1-carboxylic acid butylamide is dissolved in 9 ml of methanol in the presence of 0.1 g of palladium-on-charcoal at 10%. The reaction mixture is stirred for 4 hours under a hydrogen atmosphere. The reaction mixture is filtered. 0.14 g of 4-(2,4-dihydroxyphenyl)piperidine-1-carboxylic acid butylamide is obtained. Yield=90%.

$^1$H NMR (DMSO, 400 MHz): 0.86 (t, J=7 Hz, 3H); 1.30 (m, 2H); 1.37 (m, 4H); 1.60 (m, 2H); 2.62 (m, 2H); 2.80 (m, 1H); 3.00 (m, 2H); 4.03 (m, 2H); 6.12 (dd, J=8.4 & 2.4 Hz, 1H); 6.25 (d, J=2.4 Hz, 1H); 6.38 (t, J=5.4 Hz, 1H); 6.77 (d, J=8.2 Hz, 1H); 8.95 (s, 1H); 9.11 (s, 1H).

$^{13}$C NMR (DMSO, 100 MHz): 13.8, 19.6, 31.7, 32.0, 34.7, 44.3, 102.3, 106.0, 122.5, 126.7, 155.2, 156.0, 157.3.

EXAMPLE 13

4-(2,4-Dihydroxyphenyl)piperidine-1-carboxylic acid propylamide

In a manner analogous to Example 12a, but using propyl isocyanate, 4-(2,4-dihydroxyphenyl)piperidine-1-carboxylic acid propylamide is obtained.

$^1$H NMR (DMSO, 400 MHz): 0.86 (t, J=7 Hz, 3H); 1.37 (m, 4H); 1.59 (m, 2H); 2.65 (m, 2H); 2.79 (m, 1H); 2.97 (m, 2H); 4.03 (m, 2H); 6.12 (dd, J=8.4 & 2.4 Hz, 1H); 6.25 (d, J=2.4 Hz, 1H); 6.41 (t, J=5.4 Hz, 1H); 6.77 (d, J=8.2 Hz, 1H); 8.95 (s, 1H); 9.12 (s, 1H).

$^{13}$C NMR (DMSO, 100 MHz): 11.3, 23.0, 31.7, 34.7, 41.9, 44.3, 102.3, 106.0, 122.5, 126.7, 155.2, 156.0, 157.3.

EXAMPLE 14

1-[4-(2,4-Dihydroxyphenyl)piperidin-1-yl]butan-1-one

In a manner analogous to Example 11c, but using butanoyl chloride, 1-[4-(2,4-dihydroxyphenyl)piperidin-1-yl]butan-1-one is obtained.

$^1$H NMR (DMSO, 400 MHz): 0.86 (t, J=7.5 Hz, 3H); 1.29-1.55 (m, 4H); 1.67 (m, 2H); 2.27 (t, J=8 Hz, 2H); 2.48 (bm, 1H); 2.90 (t, J=11.6 Hz, 1H); 3.02 (t, J=12.8 Hz, 1H); 3.91 (bd, J=12.8 Hz, 1H); 4.50 (bd, J=13.2 Hz, 1H); 6.13 (dd, J=8.4 & 2.4 Hz, 1H); 6.24 (d, J=2.4 Hz, 1H); 6.77 (d, J=8.3 Hz, 1H); 8.93 (s, 1H), 9.11 (s, 1H).

$^{13}$C NMR (DMSO, 100 MHz): 14.3, 18.8, 32.1 & 32.9, 34.8, 35.1, 42.3 & 46.3, 102.8, 106.5, 122.6, 127.2, 155.6, 156.6, 170.5.

EXAMPLE 15

1-[4-(2,4-Dihydroxyphenyl)piperidin-1-yl]-2-methylpropan-1-one

In a manner analogous to Example 11c, but using 2-methylpropanoyl chloride, 1-[4-(2,4-dihydroxyphenyl)piperidin-1-yl]-2-methylpropan-1-one is obtained.

$^1$H NMR (DMSO, 400 MHz): 0.96 (2t, J=7.5 Hz, 6H); 1.28-1.46 (m, 2H); 1.68 (m, 2H); 2.51 (bm, 1H); 2.87 (m, 2H); 3.05 (t, J=12.8 Hz, 1H); 4.01 (bd, J=12.8 Hz, 1H); 4.53 (bd, J=13.2 Hz, 1H); 6.13 (dd, J=8.4 & 2.4 Hz, 1H); 6.25 (d, J=2.4 Hz, 1H); 6.79 (d, J=8.3 Hz, 1H); 8.97 (s, 1H), 9.15 (s, 1H).

$^{13}$C NMR (DMSO, 100 MHz): 19.3, 19.6, 28.9, 31.6 & 32.6, 34.7, 42.0 & 45.6, 102.3, 106.0, 122.0, 126.7, 155.2, 156.1, 173.9.

EXAMPLE 16

4-(2,4-Dihydroxyphenyl)piperidine-1-carboxylic acid phenylamide

In a manner analogous to Example 12a, but using phenyl isocyanate, 4-(2,4-dihydroxyphenyl)piperidine-1-carboxylic acid phenylamide is obtained.

$^1$H NMR (DMSO, 400 MHz): 1.46 (m, 2H); 1.70 (d, J=11.6 Hz, 2H); 2.82 (t, J=11.4 Hz, 2H); 2.90 (m, 1H); 4.23 (d, J=13.1 Hz, 2H); 6.14 (dd, J=8.4 & 2.4 Hz, 1H); 6.25 (d, J=2.4 Hz, 1H); 6.82 (d, J=8.3 Hz, 1H); 6.91 (t, J=8.2 Hz, 1H); 7.21 (t, J=8 Hz, 2H); 7.45 (d, J=8 Hz, 2H); 8.47 (s, 1H); 8.97 (s, 1H); 9.16 (s, 1H).

$^{13}$C NMR (DMSO, 100 MHz): 31.8, 34.7, 44.7, 102.4, 106.0, 119.5, 121.4, 122.3, 126.8, 128.2, 140.7, 154.9, 155.2, 156.1.

EXAMPLE 17

4-(2,4-Dihydroxyphenyl)piperidine-1-carboxylic acid (4-fluorophenyl)amide

In a manner analogous to Example 12a, but using 4-fluorophenyl isocyanate, 4-(2,4-dihydroxyphenyl)piperidine-1-carboxylic acid (4-fluorophenyl)amide is obtained.

$^1$H NMR (DMSO, 400 MHz): 1.46 (m, 2H); 1.69 (d, J=11.6 Hz, 2H); 2.82 (t, J=11.4 Hz, 2H); 2.90 (m, 1H); 4.22 (d, J=13.1 Hz, 2H); 6.14 (dd, J=8.4 & 2.4 Hz, 1H); 6.28 (d, J=2.4 Hz, 1H); 6.81 (d, J=8.3 Hz, 1H); 7.08 (t, J=8.2 Hz, 2H); 7.46 (m, 2H); 8.51 (s, 1H); 9.00 (s, 1H); 9.16 (s, 1H).

$^{13}$C NMR (DMSO, 100 MHz): 31.8, 34.7, 44.6, 102.4, 106.0, 114.6, 121.2, 122.3, 126.8, 137.0, 154.9, 155.2, 156.0, 156.1, 158.4.

EXAMPLE 18

4-(2,4-Dihydroxyphenyl)piperidine-1-carboxylic acid p-tolylamide

In a manner analogous to Example 12a, but using p-tolyl isocyanate, 4-(2,4-dihydroxyphenyl)piperidine-1-carboxylic acid p-tolylamide is obtained.

$^1$H NMR (DMSO, 400 MHz): 1.46 (m, 2H); 1.69 (d, J=11.6 Hz, 2H); 2.22 (s, 3H); 2.83 (t, J=11.4 Hz, 2H); 2.90 (m, 1H); 4.22 (d, J=13.1 Hz, 2H); 6.14 (dd, J=8.4 & 2.4 Hz, 1H); 6.27 (d, J=2.4 Hz, 1H); 6.82 (d, J=8.3 Hz, 1H); 7.02 (d, J=8.2 Hz, 2H); 7.34 (d, J=8 Hz, 2H); 8.37 (s, 1H); 8.97 (s, 1H); 9.15 (s, 1H).

$^{13}$C NMR (DMSO, 100 MHz): 20.3, 31.8, 34.7, 44.6, 102.4, 106.0, 119.7, 122.3, 126.8, 128.6, 130.2, 138.1, 154.9, 155.2, 156.1.

EXAMPLE 19

4-(2,4-Dihydroxyphenyl)piperidine-1-carboxylic acid phenethylamide

In a manner analogous to Example 12a, but using phenethyl isocyanate, 4-(2,4-dihydroxyphenyl)piperidine-1-carboxylic acid phenethylamide is obtained.

$^1$H NMR (DMSO, 400 MHz): 1.34 (m, 2H); 1.60 (d, J=11.6 Hz, 2H); 2.64-2.73 (m, 4H); 2.83 (m, 1H); 3.22 (m, 2H); 4.02 (d, J=13.1 Hz, 2H); 6.14 (dd, J=8.4 & 2.4 Hz, 1H); 6.26 (d, J=2.4 Hz, 1H); 6.54 (m, 1H); 6.78 (d, J=8.3 Hz, 1H); 7.18 (m, 3H); 7.28 (m, 2H); 8.97 (s, 1H); 9.12 (s, 1H).

$^{13}$C NMR (DMSO, 100 MHz): 31.7, 34.7, 36.0, 41.9, 44.3, 102.4, 106.0, 122.5, 125.8, 126.7, 128.2, 128.6, 139.9, 155.4, 1, 156.0, 157.2.

EXAMPLE 20

4-(2,4-Dihydroxyphenyl)piperidine-1-carboxylic acid (3-fluorophenyl)amide

In a manner analogous to Example 12a, but using 3-fluorophenyl isocyanate, 4-(2,4-dihydroxyphenyl)piperidine-1-carboxylic acid (3-fluorophenyl)amide is obtained.

$^1$H NMR (DMSO, 400 MHz): 1.46 (m, 2H); 1.69 (d, J=11.6 Hz, 2H); 2.82 (t, J=11.4 Hz, 2H); 2.90 (m, 1H); 4.22 (d, J=13.1 Hz, 2H); 6.14 (dd, J=8.4 & 2.4 Hz, 1H); 6.27 (d, J=2.4 Hz, 1H); 6.70 (m, 1H); 6.81 (d, J=8.3 Hz, 1H); 7.24 (m, 2H); 7.47 (d, J=18 Hz, 1H); 8.70 (s, 1H); 9.00 (s, 1H); 9.17 (s, 1H).

$^{13}$C NMR (DMSO, 100 MHz): 31.8, 34.7, 44.7, 102.4, 106.0, 107.6, 114.9, 122.2, 126.8, 129.6, 142.7, 154.5, 155.2, 156.1, 162.1.

EXAMPLE 21

4-(2,4-Dihydroxyphenyl)piperidine-1-carboxylic acid ((R)-1-phenylethyl)amide In a manner analogous to Example 12a, but using ((R)-1-isocyanatoethyl)benzene, 4-(2,4-dihydroxyphenyl)piperidine-1-carboxylic acid ((R)-1-phenylethyl)amide is obtained.

$^1$H NMR (DMSO, 400 MHz): 1.35 (d, J=7.1 Hz, 3H); 1.38 (m, 2H); 1.62 (m, 2H); 2.82 (t, J=13 Hz, 2H); 2.83 (m, 1H); 4.22 (d, J=12.3 Hz, 2H); 4.84 (m, 1H); 6.13 (dd, J=8.4 & 2.4 Hz, 1H); 6.26 (d, J=2.4 Hz, 1H); 6.73 (d, J=7.9 Hz, 1H); 6.78 (d, J=8.3 Hz, 1H); 7.18 (m, 1H); 7.32 (m, 4H); 8.96 (s, 1H); 9.13 (s, 1H).

$^{13}$C NMR (DMSO, 100 MHz): 22.8, 31.7, 31.8, 44.4, 49.3, 102.4, 106.0, 122.5, 125.9, 126.1, 126.7, 127.9, 146.3, 155.2, 156.0, 156.6.

EXAMPLE 22

4-(2,4-Dihydroxyphenyl)piperidine-1-carboxylic acid methylphenylamide $^1$H NMR (DMSO, 400 MHz): 1.28 (m, 2H); 1.48 (d, J=12 Hz, 2H); 2.62 (t, J=12.6 Hz, 2H); 2.77 (m, 1H); 3.09 (s, 3H); 3.80 (d, J=13 Hz, 2H); 6.13 (dd, J=8.4 & 2.4 Hz, 1H); 6.22 (d, J=2.4 Hz, 1H); 6.70 (d, J=7.9 Hz, 1H); 7.11 (m, 3H); 7.35 (m, 2H); 8.96 (s, 1H); 9.09 (s, 1H).

$^{13}$C NMR (DMSO, 100 MHz): 31.2, 34.4, 38.8, 46.0, 102.3, 106.0, 122.2, 122.6, 123.6, 126.6, 129.2, 146.7, 155.1, 156.0, 160.0.

EXAMPLE 23

4-(2,4-Dihydroxyphenyl)piperidine-1-carboxylic acid pyridin-2-ylamide a) Pyridin-2-ylcarbamic acid 4-nitrophenyl ester 0.5 g of 2-aminopyridine is dissolved in 10 ml of dichloromethane and then 1.18 g of 4-nitrophenyl chloroformate are added, as are 1.85 ml of N,N-diisopropylethylamine. The reaction mixture is stirred for one hour at ambient temperature. 50 ml of water are added to the reaction mixture and then the medium is extracted with 50 ml of dichloromethane. The solvents are evaporated off and then the solid is used in the next stage without further purification.

b) 4-(2,4-Bis(benzyloxy)phenyl)piperidine-1-carboxylic acid pyridin-2-ylamide 0.5 g of 4-(2,4-bis(benzyloxy)phenyl)piperidinium chloride is suspended in 5 ml of dimethylformamide and then 0.43 ml of N,N-diisopropylethylamine is added, as is 0.38 g of pyridin-2-ylcarbamic acid 4-nitrophenyl ester in solution in 2 ml of dimethylformamide. The reaction mixture is stirred for 24 hours at 80° C. It is heated at 80° C. for 24 hours. 50 ml of water are added, and the reaction mixture is then extracted with 50 ml of ethyl acetate. The solvents are evaporated off and then the residue is chromatographed on silica gel (70/30 heptane/ethyl acetate). 20 mg of 4-(2,4-bis(benzyloxy)phenyl)piperidine-1-carboxylic acid pyridin-2-ylamide are obtained.

c) 4-(2,4-Dihydroxyphenyl)piperidine-1-carboxylic acid pyridin-2-ylamide 20 mg of 4-(2,4-Bis(benzyloxy)phenyl)piperidine-1-carboxylic acid pyridin-2-ylamide are dissolved in 20 ml of ethyl acetate and then 1 ml of methanol is added. 10 mg of palladium-on-charcoal at 10% are added, and then the reaction mixture is stirred for 18 hours under a hydrogen atmosphere. The mixture is filtered and the residue is then crystallized from an ethyl acetate/heptane mixture. 5 mg of 4-(2,4-dihydroxyphenyl)piperidine-1-carboxylic acid pyridin-2-ylamide. Yield: 39%

$^1$H NMR (DMSO, 400 MHz): 1.458 (m, 2H); 1.68 (m, 2H); 2.85 (m, 3H); 4.26 (d, J=13.6 Hz, 2H); 6.14 (dd, J=8.4 & 2.4 Hz, 1H); 6.25 (d, J=2.4 Hz, 1H); 6.81 (d, J=7.9 Hz, 1H); 6.95 (m, 1H); 7.66 (m, 1H); 7.78 (d, J=7.9 Hz, 1H); 8.21 (m, 1H); 8.97 (s, 1H); 9.09 (s, 1H), 9.15 (s, 1H).

EXAMPLE 24

4-(2,4-Dihydroxyphenyl)piperidine-1-carboxylic acid ((S)-1-phenylethyl)amide In a manner analogous to Example 12a, but using ((S)-1-isocyanatoethyl)benzene, 4-(2,4-dihydroxyphenyl)piperidine-1-carboxylic acid ((S)-1-phenylethyl)amide is obtained.

$^1$H NMR (DMSO, 400 MHz): 1.35 (d, J=7.1 Hz, 3H); 1.38 (m, 2H); 1.62 (m, 2H); 2.82 (t, J=13 Hz, 2H); 2.83 (m, 1H); 4.22 (d, J=12.3 Hz, 2H); 4.84 (m, 1H); 6.13 (dd, J=8.4 & 2.4 Hz, 1H); 6.26 (d, J=2.4 Hz, 1H); 6.73 (d, J=7.9 Hz, 1H); 6.78 (d, J=8.3 Hz, 1H); 7.18 (m, 1H); 7.32 (m, 4H); 8.96 (s, 1H); 9.09 (s, 1H).

$^{13}$C NMR (DMSO, 100 MHz): 22.8, 31.7, 31.8, 44.4, 49.3, 102.4, 106.0, 122.5, 125.9, 126.1, 126.7, 127.9, 146.3, 155.2, 156.0, 156.6.

EXAMPLE 25

4-(2,4-Dihydroxyphenyl)piperidine-1-carboxylic acid ((S)-1-phenylpropyl)amide In a manner analogous to Example 12a, but using ((S)-1-isocyanatopropyl)benzene, 4-(2,4-dihydroxyphenyl)piperidine-1-carboxylic acid ((S)-1-phenylpropyl)amide is obtained.

$^1$H NMR (DMSO, 400 MHz): 0.82 (t, J=7.1 Hz, 3H); 1.37 (m, 2H); 1.67 (m, 4H); 2.67 (m, 2H); 2.83 (m, 1H); 4.12 (d, J=12.3 Hz, 2H); 4.56 (m, 1H); 6.13 (dd, J=8.4 & 2.4 Hz, 1H); 6.26 (d, J=2.4 Hz, 1H); 6.65 (d, J=7.9 Hz, 1H); 6.77 (d, J=8.3 Hz, 1H); 7.18 (m, 1H); 7.29 (m, 4H); 8.96 (s, 1H); 9.11 (s, 1H).

$^{13}$C NMR (DMSO, 100 MHz): 11.4, 29.3, 31.7, 34.7, 44.5, 55.8, 102.4, 106.0, 122.5, 126.1, 126.4, 126.7, 127.9, 145.4, 155.1, 156.0, 156.9.

EXAMPLE 26

(R)-2-Amino-1-[4-(2,4-dihydroxyphenyl)piperidin-1-yl]-3-phenylpropan-1-one a) {(R)-1-Benzyl-2-[4-(2,4-bis(benzyloxy)phenyl)piperidin-1-yl]-2-oxoethyl}carbamic acid benzyl ester In a 50 ml round-bottomed flask, 0.615 g of Z-L-phenylalanine is dissolved in 10 ml of dimethylformamide, and 0.43 g of 1-(3-dimethylaminopropyl)-3-ethylcarbodiimide (EDC) and also 0.305 g of 1-hydroxybenzotriazole (HOBT) are added, and the reaction mixture is then stirred for 5 minutes at ambient temperature.

1 g of 4-(2,4-bis(benzyloxy)phenyl)piperidinium hydrochloride and also 0.36 ml of diisopropylamine are added. The reaction mixture is stirred for 1 hour at ambient temperature. The reaction medium is washed with 20 ml of 5% citric acid and then extracted with 20 ml of ethyl acetate, the organic phase is washed with 20 ml of a 1M solution of sodium hydroxide, and the organic phase is dried over magnesium sulphate. After evaporation of the solvents, the crude product is chromatographed on silica gel. 1.23 g of {(R)-1-benzyl-2-[4-(2,4-bis(benzyloxy)phenyl)piperidin-1-yl]-2-oxoethyl}carbamic acid benzyl ester are obtained.

b) (R)-2-Amino-1-[4-(2,4-dihydroxyphenyl) piperidin-1-yl]-3-phenylpropan-1-one In a 25 ml round-bottomed flask, 1.23 g of {(R)-1-benzyl-2-[4-(2,4-bis(benzyloxy)phenyl)piperidin-1-yl]-2-oxoethyl}carbamic acid benzyl ester are dissolved in 15 ml of methanol and also 15 ml of ethyl acetate in the presence of 0.25 g of palladium-on-charcoal at 10%. The reaction mixture is stirred for 18 hours under a hydrogen atmosphere. The reaction mixture is filtered. The residue is chromatographed on silica gel (95/5 dichloromethane/methanol). 0.625 g of (R)-2-amino-1-[4-(2,4-dihydroxyphenyl)piperidin-1-yl]-3-phenylpropan-1-one is obtained. Yield=64%.

$^1$H NMR (DMSO, 400 MHz): 0.6 (m, 1H); 1.09 (m, 1H); 1.30-1.75 (m, 5H); 2.56-2.97 (m, 4H); 3.94 (m, 2H); 4.51 (d, J=12.8 Hz, 1H); 6.11 (m, 1H); 6.24 (m, 1H); 6.57 & 6.77 (d, J=8.3 Hz, 1H); 7.18-7.40 (m, 5H); 8.97 (s, 1H); 9.11 & 9.15 (s, 1H).

$^{13}$C NMR (DMSO, 100 MHz): (hindrance of rotation) 31.6, 32.3, 31.1, 34.6, 42.0, 42.2, 42.7, 45.3, 45.6, 51.3, 51.6, 102.3, 105.9, 121.9, 126.0, 126.7, 127.9, 128.1, 129.4, 138.5, 155.0, 156.0, 172.6.

EXAMPLE 27

1-[4-(2,4-Dihydroxyphenyl)piperidin-1-yl]-3-phenylpropan-1-one

In a manner analogous to Example 11c, but using 3-phenylpropionyl chloride, 1-[4-(2,4-dihydroxyphenyl)piperidin-1-yl]-3-phenylpropan-1-one is obtained.

$^1$H NMR (DMSO, 400 MHz): 1.33 (m, 2H); 1.63 (m, 2H); 2.50-2.70 (m, 3H); 2.80-3.0 (m, 4H); 3.92 (d, J=12.8 Hz, 1H); 4.53 (d, J=12.8 Hz, 1H); 6.14 (dd, J=8.4 & 2.4 Hz, 1H); 6.26 (d, J=2.4 Hz, 1H); 6.75 (d, J=7.9 Hz, 1H); 7.15-7.29 (m, 5H); 8.97 (s, 1H); 9.11 (s, 1H).

$^{13}$C NMR (DMSO, 100 MHz): 30.9, 31.6, 32.2, 33.9, 34.5, 42.0, 45.8, 102.4, 106.0, 122.1, 125.8, 126.7, 128.2, 128.4, 141.5, 155.2, 156.1, 169.5.

EXAMPLE 28

4-(2,4-Dihydroxyphenyl)piperidine-1-carboxylic acid 2-fluorobenzylamide

In a manner analogous to Example 12a, but using 2-fluorobenzyl isocyanate, 4-(2,4-dihydroxyphenyl)piperidine-1-carboxylic acid 2-fluorobenzylamide is obtained.

$^1$H NMR (DMSO, 400 MHz): 1.40 (m, 2H); 1.63 (m, 2H); 2.76 (t, J=13 Hz, 2H); 2.84 (m, 1H); 4.02 (d, J=12.3 Hz, 2H); 4.28 (d, J=5.5 Hz, 2H); 6.14 (dd, J=8.4 & 2.4 Hz, 1H); 6.26 (d, J=2.4 Hz, 1H); 6.73 (d, J=7.9 Hz, 1H); 7.03 (t, J=5.6 Hz, 1H); 7.16 (m, 2H); 7.28 (m, 2H); 8.96 (s, 1H); 9.13 (s, 1H).

$^{13}$C NMR (DMSO, 100 MHz): 31.7, 34.7, 37.0, 44.4, 102.4, 106.0, 114.7, 122.4, 124.1, 126.7, 127.7, 128.2, 129.0, 155.2, 156.0, 157.2, 158.6, 161.0

EXAMPLE 29

4-(2,4-Dihydroxyphenyl)piperidine-1-carboxylic acid 3-fluorobenzylamide

In a manner analogous to Example 12a, but using 3-fluorobenzyl isocyanate, 4-(2,4-dihydroxyphenyl)piperidine-1-carboxylic acid 3-fluorobenzylamide is obtained.

$^1$H NMR (DMSO, 400 MHz): 1.38 (m, 2H); 1.63 (m, 2H); 2.73 (t, J=13 Hz, 2H); 2.86 (m, 1H); 4.04 (d, J=12.3 Hz, 2H); 4.23 (d, J=5.5 Hz, 2H); 6.14 (dd, J=8.4 & 2.4 Hz, 1H); 6.26 (d, J=2.4 Hz, 1H); 6.79 (d, J=7.9 Hz, 1H); 7.06 (m, 4H); 7.34 (m, 1H); 8.96 (s, 1H); 9.13 (s, 1H).

$^{13}$C NMR (DMSO, 100 MHz): 31.8, 24.7, 43.1, 44.5, 102.5, 106.1, 113.0 & 113.2, 113.5 & 113.7, 122.5, 123.0, 126.8, 130.0, 144.6, 155.3, 156.1, 157.3.

EXAMPLE 30

4-(2,4-Dihydroxyphenyl)piperidine-1-carboxylic acid 4-fluorobenzylamide

In a manner analogous to Example 12a, but using 4-fluorobenzyl isocyanate, 4-(2,4-dihydroxyphenyl)piperidine-1-carboxylic acid 4-fluorobenzylamide is obtained.

$^1$H NMR (DMSO, 400 MHz): 1.38 (m, 2H); 1.63 (m, 2H); 2.71 (t, J=13 Hz, 2H); 2.84 (m, 1H); 4.04 (d, J=12.3 Hz, 2H); 4.21 (d, J=5.5 Hz, 2H); 6.14 (dd, J=8.4 & 2.4 Hz, 1H); 6.26 (d,

J=2.4 Hz, 1H); 6.78 (d, J=7.9 Hz, 1H); 7.05 (t, J=5.6 Hz, 1H); 7.13 (m, 2H); 7.28 (m, 2H); 8.96 (s, 1H); 9.13 (s, 1H).

$^{13}$C NMR (DMSO, 100 MHz): 31.7, 34.7, 42.8, 44.4, 102.4, 106.0, 114.7, 122.4, 126.7, 128.8, 137.4, 155.2, 156.0, 157.2, 159.7 & 162.1.

EXAMPLE 31

4-(2,4-Dihydroxyphenyl)piperidine-1-carboxylic acid benzylamide

In a manner analogous to Example 12a, but using benzyl isocyanate, 4-(2,4-dihydroxyphenyl)piperidine-1-carboxylic acid benzylamide is obtained.

$^{1}$H NMR (DMSO, 400 MHz): 1.41 (m, 2H); 1.63 (m, 2H); 2.72 (t, J=13 Hz, 2H); 2.85 (m, 1H); 4.02 (d, J=12.3 Hz, 2H); 4.24 (d, J=5.5 Hz, 2H); 6.14 (dd, J=8.4 & 2.4 Hz, 1H); 6.26 (d, J=2.4 Hz, 1H); 6.79 (d, J=7.9 Hz, 1H); 7.05 (t, J=5.6 Hz, 1H); 7.24 (m, 5H); 7.28 (m, 2H); 8.96 (s, 1H); 9.13 (s, 1H).

$^{13}$C NMR (DMSO, 100 MHz): 31.7, 34.7, 43.5, 44.4, 102.4, 106.0, 122.4, 126.3, 126.7, 126.9, 128.0, 141.2, 155.2, 156.0, 157.3.

EXAMPLE 32

4-(2,4-Dihydroxyphenyl)piperidine-1-carboxylic acid 2-methylbenzylamide

In a manner analogous to Example 12a, but using 2-methylbenzyl isocyanate, 4-(2,4-dihydroxyphenyl)piperidine-1-carboxylic acid 2-methylbenzylamide is obtained.

$^{1}$H NMR (DMSO, 400 MHz): 1.40 (m, 2H); 1.62 (m, 2H); 2.27 (s, 3H); 2.73 (t, J=13 Hz, 2H); 2.85 (m, 1H); 4.10 (d, J=12.3 Hz, 2H); 4.22 (d, J=5.5 Hz, 2H); 6.14 (dd, J=8.4 & 2.4 Hz, 1H); 6.26 (d, J=2.4 Hz, 1H); 6.79 (d, J=7.9 Hz, 1H); 6.90 (t, J=5.6 Hz, 1H); 7.09-7.20 (m, 4H); 7.28 (m, 2H); 9 (bs, 1H); 9.12 (bs, 1H).

$^{13}$C NMR (DMSO, 100 MHz): 18.6, 31.8, 34.7, 41.4, 44.5, 102.4, 106.0, 122.4, 125.5, 126.2, 126.7, 126.9, 129.6, 135.0, 138.7, 155.2, 156.0, 157.3.

EXAMPLE 33

4-(2,4-Dihydroxyphenyl)piperidine-1-carboxylic acid 3-methylbenzylamide

In a manner analogous to Example 12a, but using 3-methylbenzyl isocyanate, 4-(2,4-dihydroxyphenyl)piperidine-1-carboxylic acid 3-methylbenzylamide is obtained.

$^{1}$H NMR (DMSO, 400 MHz): 1.40 (m, 2H); 1.62 (m, 2H); 2.28 (s, 3H); 2.72 (t, J=13 Hz, 2H); 2.86 (m, 1H); 4.02 (d, J=12.3 Hz, 2H); 4.20 (d, J=5.5 Hz, 2H); 6.14 (dd, J=8.4 & 2.4 Hz, 1H); 6.26 (d, J=2.4 Hz, 1H); 6.78 (d, J=7.9 Hz, 1H); 7.00-7.06 (m, 4H); 7.18 (t, J=7.6 Hz, 1H); 8.99 (s, 1H); 9.13 (s, 1H).

$^{13}$C NMR (DMSO, 100 MHz): 21.0, 31.7, 34.7, 43.4, 44.5, 102.4, 106.0, 122.5, 124.1, 126.7, 126.9, 127.6, 127.9, 136.9, 141.1, 155.2, 156.0, 157.3.

EXAMPLE 34

4-(2,4-Dihydroxyphenyl)piperidine-1-carboxylic acid 4-methylbenzylamide

In a manner analogous to Example 12a, but using 4-methylbenzyl isocyanate, 4-(2,4-dihydroxyphenyl)piperidine-1-carboxylic acid 4-methylbenzylamide is obtained.

$^{1}$H NMR (DMSO, 400 MHz): 1.41 (m, 2H); 1.62 (m, 2H); 2.27 (s, 3H); 2.71 (t, J=13 Hz, 2H); 2.84 (m, 1H); 4.08 (d, J=12 Hz, 2H); 4.19 (d, J=5.5 Hz, 2H); 6.14 (dd, J=8.4 & 2.4 Hz, 1H); 6.26 (d, J=2.4 Hz, 1H); 6.78 (d, J=7.9 Hz, 1H); 6.99 (t, J=5.6 Hz, 1H); 7.12 (2d, J=8 Hz, 4H); 8.96 (s, 1H); 9.13 (s, 1H).

$^{13}$C NMR (DMSO, 100 MHz): 20.8, 31.9, 34.9, 43.4, 44.6, 102.6, 106.2, 122.7, 126.9, 127.2, 128.7, 135.4, 138.4, 155.4, 156.3, 157.5.

EXAMPLE 35

4-(2,4-Dihydroxyphenyl)piperidine-1-carboxylic acid 2-methoxybenzylamide

In a manner analogous to Example 12a, but using 2-methoxybenzyl isocyanate, 4-(2,4-dihydroxyphenyl)piperidine-1-carboxylic acid 2-methoxybenzylamide is obtained.

$^{1}$H NMR (DMSO, 400 MHz): 1.41 (m, 2H); 1.63 (m, 2H); 2.74 (t, J=13 Hz, 2H); 2.86 (m, 1H); 3.79 (s, 3H); 4.11 (d, J=12.3 Hz, 2H); 4.22 (d, J=5.5 Hz, 2H); 6.14 (dd, J=8.4 & 2.4 Hz, 1H); 6.26 (d, J=2.4 Hz, 1H); 6.79-6.95 (m, 4H); 7.13-7.22 (m, 2H); 9.00 (bs, 1H); 9.14 (bs, 1H).

$^{13}$C NMR (DMSO, 100 MHz): 31.7, 34.7, 38.3, 44.5, 55.2, 102.4, 106.0, 110.1, 119.9, 122.5, 126.7, 126.9, 127.3, 128.6, 155.2, 156.1, 156.3, 157.4.

EXAMPLE 36

4-(2,4-Dihydroxyphenyl)piperidine-1-carboxylic acid 3-methoxybenzylamide

In a manner analogous to Example 12a, but using 3-methoxybenzyl isocyanate, 4-(2,4-dihydroxyphenyl)piperidine-1-carboxylic acid 3-methoxybenzylamide is obtained.

$^{1}$H NMR (DMSO, 400 MHz): 1.41 (m, 2H); 1.63 (m, 2H); 2.72 (t, J=13 Hz, 2H); 2.86 (m, 1H); 3.73 (s, 3H); 4.09 (d, J=12.3 Hz, 2H); 4.21 (d, J=5.5 Hz, 2H); 6.14 (dd, J=8.4 & 2.4 Hz, 1H); 6.26 (d, J=2.4 Hz, 1H); 6.79 (m, 4H); 7.03 (t, J=5.6 Hz, 1H); 7.22 (t, J=8 Hz, 1H); 9.02 (bs, 1H); 9.10 (bs, 1H).

$^{13}$C NMR (DMSO, 100 MHz): 31.7, 34.7, 43.4, 44.5, 54.9, 102.4, 106.0, 111.6, 112.6, 119.1, 122.5, 126.7, 129.0, 142.9, 155.2, 156.0, 157.3, 159.2.

EXAMPLE 37

4-(2,4-Dihydroxyphenyl)piperidine-1-carboxylic acid 4-methoxybenzylamide

In a manner analogous to Example 12a, but using 4-methoxybenzyl isocyanate, 4-(2,4-dihydroxyphenyl)piperidine-1-carboxylic acid 4-methoxybenzylamide is obtained.

$^{1}$H NMR (DMSO, 400 MHz): 1.41 (m, 2H); 1.62 (m, 2H); 2.70 (t, J=13 Hz, 2H); 2.84 (m, 1H); 3.72 (s, 3H); 4.08 (d, J=12 Hz, 2H); 4.16 (d, J=5.5 Hz, 2H); 6.14 (dd, J=8.4 & 2.4 Hz, 1H); 6.26 (d, J=2.4 Hz, 1H); 6.78 (d, J=7.9 Hz, 1H); 6.87 (d, J=8 Hz, 2H); 7.12 (t, J=5.6 Hz, 1H); 7.18 (d, J=8 Hz, 2H); 9.06 (s, 2H).

$^{13}$C NMR (DMSO, 100 MHz): 31.7, 34.7, 42.9, 44.4, 55.0, 102.4, 106.0, 113.4, 122.4, 126.7, 128.3, 133.2, 155.2, 156.1, 157.3, 157.9.

EXAMPLE 38

4-(2,4-Dihydroxyphenyl)piperidine-1-carboxylic acid ((S)-1-p-tolylethyl)amide

In a manner analogous to Example 12a, but using ((S)-1-isocyanatoethyl)-4-methylbenzene, 4-(2,4-dihydroxyphenyl)piperidine-1-carboxylic acid ((S)-1-p-tolylethyl)amide is obtained.

$^1$H NMR (DMSO, 400 MHz): 1.35 (d, J=7.1 Hz, 3H); 1.38 (m, 2H); 1.62 (m, 2H); 2.26 (s, 3H); 2.67 (t, J=13 Hz, 2H); 2.83 (m, 1H); 4.11 (d, J=12.3 Hz, 2H); 4.84 (m, 1H); 6.14 (dd, J=8.4 & 2.4 Hz, 1H); 6.26 (d, J=2.4 Hz, 1H); 6.67 (d, J=7.9 Hz, 1H); 6.77 (d, J=8.3 Hz, 1H); 7.09 (d, J=8 Hz, 2H); 7.20 (d, J=8 Hz, 2H); 8.96 (s, 1H); 9.12 (s, 1H).

$^{13}$C NMR (DMSO, 100 MHz): 18.5, 20.6, 22.9, 31.8, 34.7, 44.4, 49.0, 102.4, 106.0, 122.5, 125.8, 126.7, 128.5, 135.0, 143.2, 155.2, 156.0, 156.6.

EXAMPLE 39

4-(2,4-Dihydroxyphenyl)piperidine-1-carboxylic acid [(S)-1-(4-fluorophenyl)ethyl]amide In a manner analogous to Example 12a, but using 1-fluoro-4-((S)-1-isocyanatoethyl)benzene, 4-(2,4-dihydroxyphenyl)piperidine-1-carboxylic acid [(S)-1-(4-fluorophenyl)ethyl]amide is obtained.

$^1$H NMR (DMSO, 400 MHz): 1.35 (d, J=7.1 Hz, 3H); 1.38 (m, 2H); 1.62 (m, 2H); 2.67 (t, J=13 Hz, 2H); 2.83 (m, 1H); 4.09 (d, J=12.3 Hz, 2H); 4.84 (m, 1H); 6.14 (dd, J=8.4 & 2.4 Hz, 1H); 6.26 (d, J=2.4 Hz, 1H); 6.74 (d, J=7.9 Hz, 1H); 6.78 (d, J=8.3 Hz, 1H); 7.09 (t, J=8.9 Hz, 2H); 7.35 (m, 2H); 8.96 (s, 1H); 9.12 (s, 1H).

$^{13}$C NMR (DMSO, 100 MHz): 22.8, 31.7, 34.7, 44.4, 48.7, 102.4, 106.0, 114.5, 122.4, 126.7, 127.8, 142.4, 155.2, 156.0, 156.5, 160.7 (d, J=241 Hz).

EXAMPLE 40

4-(2,4-Dihydroxyphenyl)piperidine-1-carboxylic acid (S)-indan-1-ylamide

In a manner analogous to Example 12a, but using (S)-1-isocyanatoindane, 4-(2,4-dihydroxyphenyl)piperidine-1-carboxylic acid (S)-indan-1-ylamide is obtained.

$^1$H NMR (DMSO, 400 MHz): 1.38 (m, 2H); 1.62 (m, 2H); 1.86 (m, 1H); 2.36 (m, 1H); 2.68-2.93 (m, 5H); 4.13 (d, J=12.3 Hz, 2H); 5.23 (m, 1H); 6.14 (dd, J=8.4 & 2.4 Hz, 1H); 6.26 (d, J=2.4 Hz, 1H); 6.71 (d, J=7.9 Hz, 1H); 6.80 (d, J=8.3 Hz, 1H); 7.20 (m, 4H); 9.07 (bs, 2H).

$^{13}$C NMR (DMSO, 100 MHz): 29.6, 31.7, 33.2, 34.7, 44.5, 55.3, 102.4, 106.0, 122.5, 123.9, 124.3, 126.1, 126.7, 126.9, 142.6, 145.4, 155.2, 156.0, 157.4.

EXAMPLE 41

4-(2,4-Dihydroxyphenyl)piperidine-1-carboxylic acid ((S)-1-naphthalen-1-ylethyl)amide In a manner analogous to Example 12a, but using 1-((S)-1-isocyanatoethyl)naphthalene, 4-(2,4-dihydroxyphenyl)piperidine-1-carboxylic acid ((S)-1-naphthalen-1-ylethyl)amide is obtained.

$^1$H NMR (DMSO, 400 MHz): 1.37 (m, 2H); 1.49 (d, J=7.1 Hz, 3H); 1.62 (m, 2H); 2.70 (t, J=13 Hz, 2H); 2.84 (m, 1H); 4.14 (t, J=12 Hz, 2H); 5.66 (m, 1H); 6.13 (dd, J=8.4 & 2.4 Hz, 1H); 6.26 (d, J=2.4 Hz, 1H); 6.75 (d, J=7.9 Hz, 1H); 6.91 (d, J=7.7 Hz, 1H); 7.53 (m, 4H); 7.79 (d, J=8 Hz, 1H); 7.93 (d, J=8 Hz, 1H); 8.16 (d, J=8 Hz, 1H); 8.97 (s, 1H); 9.13 (s, 1H).

$^{13}$C NMR (DMSO, 100 MHz): 22.0, 31.7, 34.6, 44.6, 45.5, 102.4, 106.0, 122.2, 122.5, 123.3, 125.3, 125.4, 125.9, 126.7, 126.7, 128.5, 130.4, 133.3, 141.8, 155.2, 156.0, 156.5.

EXAMPLE 42

4-(2,4-Dihydroxyphenyl)piperidine-1-carboxylic acid ((S)-1-naphthalen-2-ylethyl)amide In a manner analogous to Example 23a, but using (S)-1-naphthalen-2-ylethylamine, and then repeating the sequence 23b and 23c, 4-(2,4-dihydroxyphenyl)piperidine-1-carboxylic acid ((S)-1-naphthalen-2-ylethyl)amide is obtained.

$^1$H NMR (DMSO, 400 MHz): 1.35 (m, 2H); 1.46 (d, J=7.1 Hz, 3H); 1.62 (m, 2H); 2.70 (t, J=13 Hz, 2H); 2.85 (m, 1H); 4.14 (d, J=12.9 Hz, 2H); 5.01 (m, 1H); 6.13 (dd, J=8.4 & 2.4 Hz, 1H); 6.26 (d, J=2.4 Hz, 1H); 6.77 (d, J=7.9 Hz, 1H); 6.85 (d, J=7.7 Hz, 1H); 7.43-7.50 (m, 3H); 7.77 (s, 1H); 7.85 (m, 3H); 8.97 (s, 1H); 9.13 (s, 1H).

$^{13}$C NMR (DMSO, 100 MHz): 22.6, 31.2, 34.6, 44.5, 49.5, 102.4, 106.0, 122.5, 123.8, 125.1, 125.3, 125.9, 126.7, 127.4, 127.5, 131.9, 132.8, 143.8, 155.2, 156.0, 156.7.

EXAMPLE 43

4-(2,4-Dihydroxyphenyl)piperidine-1-carboxylic acid [(S)-1-(4-methoxyphenyl)ethyl]amide In a manner analogous to Example 12a, but using 1-((S)-1-isocyanatoethyl)-4-methoxybenzene, 4-(2,4-dihydroxyphenyl)piperidine-1-carboxylic acid [(S)-1-(4-methoxyphenyl)ethyl]amide is obtained.

$^1$H NMR (DMSO, 400 MHz): 1.33 (d, J=7.1 Hz, 3H); 1.38 (m, 2H); 1.62 (m, 2H); 2.66 (t, J=13 Hz, 2H); 2.83 (m, 1H); 3.72 (s, 3H); 4.06 (d, J=12.3 Hz, 2H); 4.79 (m, 1H); 6.13 (dd, J=8.4 & 2.4 Hz, 1H); 6.26 (d, J=2.4 Hz, 1H); 6.64 (d, J=7.9 Hz, 1H); 6.78 (d, J=8.3 Hz, 1H); 6.85 (d, J=8.6 Hz, 2H); 7.23 (d, J=8.6 Hz, 2H); 8.96 (s, 1H); 9.13 (s, 1H).

$^{13}$C NMR (DMSO, 100 MHz): 22.9, 31.7, 34.7, 44.4, 48.6, 55.0, 102.4, 106.0, 113.3, 122.5, 126.7, 127.0, 138.2, 155.2, 156.0, 156.6, 157.7.

EXAMPLE 44

4-(2,4-Dihydroxyphenyl)piperidine-1-carboxylic acid [(S)-1-(3-methoxyphenyl)ethyl]amide In a manner analogous to Example 12a, but using 1-((S)-1-isocyanatoethyl)-3-methoxybenzene, 4-(2,4-dihydroxyphenyl)piperidine-1-carboxylic acid [(S)-1-(3-methoxyphenyl)ethyl]amide is obtained.

$^1$H NMR (DMSO, 400 MHz): 1.33 (d, J=7.1 Hz, 3H); 1.38 (m, 2H); 1.62 (m, 2H); 2.68 (t, J=13 Hz, 2H); 2.84 (m, 1H); 3.73 (s, 3H); 4.10 (d, J=12.3 Hz, 2H); 4.81 (m, 1H); 6.13 (dd, J=8.4 & 2.4 Hz, 1H); 6.26 (d, J=2.4 Hz, 1H); 6.70-6.79 (m, 5H); 7.20 (t, J=8.1 Hz, 1H); 8.96 (s, 1H); 9.13 (s, 1H).

$^{13}$C NMR (DMSO, 100 MHz): 22.9, 31.8, 34.6, 44.4, 49.3, 54.9, 102.4, 106.0, 111.3, 111.8, 118.2, 122.5, 126.7, 129.0, 148.0, 155.2, 156.0, 156.7, 159.1.

EXAMPLE 45

(S)-2-Amino-1-[4-(2,4-dihydroxyphenyl)piperidin-1-yl]-3-phenylpropan-1-one

In a manner analogous to Example 26, but using Z-D-phenylalanine, (S)-2-amino-1-[4-(2,4-dihydroxyphenyl)piperidin-1-yl]-3-phenylpropan-1-one is obtained.

$^1$H NMR (DMSO, 400 MHz): 0.6 (m, 1H); 1.09 (m, 1H); 1.30-1.75 (m, 5H); 2.56-2.97 (m, 4H); 3.94 (m, 2H); 4.51 (d, J=12.8 Hz, 1H); 6.11 (m, 1H); 6.24 (m, 1H); 6.57 & 6.77 (d, J=8.3 Hz, 1H); 7.18-7.40 (m, 5H); 8.97 (s, 1H); 9.11 & 9.15 (s, 1H).

$^{13}$C NMR (DMSO, 100 MHz): (hindrance of rotation) 31.6, 32.3, 31.1, 34.6, 42.0, 42.2, 42.7, 45.3, 45.6, 51.3, 51.6, 102.3, 105.9, 121.9, 126.0, 126.7, 127.9, 128.1, 129.4, 138.5, 155.0, 156.0, 172.6.

EXAMPLE 46

4-(5-Fluoro-2,4-dihydroxyphenyl)piperidine-1-carboxylic acid ((S)-1-phenylethyl)amide a) 1,5-Bis(benzyloxy)-2-fluoro-4-nitrobenzene 2.82 g (70.6 mmol, 2.5 eq) of sodium hydride at 60% are added to a solution of 7.6 g (70.6 mmol, 2.5 eq) of benzyl alcohol in 100 ml of tetrahydrofuran. The reaction medium is stirred at ambient temperature for 1½ hours and then 5.0 g (28.2 mmol, 1 eq) of 1,2,4-trifluoro-5-nitrobenzene in solution in 50 ml of tetrahydrofuran are added dropwise. The reaction medium is refluxed for 3 hours. The reaction medium is treated with 150 ml of 1M hydrochloric acid and extracted with ethyl acetate. The organic phases are combined, washed with a saturated solution of sodium chloride, dried over magnesium sulphate, filtered and evaporated. The residue is chromatographed on silica gel, elution being carried out with 90/10 heptane/ethyl acetate.

1.68 g of 1,5-bis(benzyloxy)-2-fluoro-4-nitrobenzene are obtained.

Yield=17%.

b) 1,5-Bis(benzyloxy)-2-fluoro-4-aminobenzene 508 mg (9.5 mmol, 2 eq) of ammonium chloride, followed by 2.23 g (34.2 mmol, 7.2 eq) of zinc powder, are added to a solution of 1.68 g (4.75 mmol, 1 eq) of 1,5-bis(benzyloxy)-2-fluoro-4-nitrobenzene in 50 ml of water. The reaction medium is refluxed for 4 hours. The cooled reaction medium is extracted with ethyl acetate. The organic phases are combined, washed with a saturated solution of sodium chloride, dried over magnesium sulphate, filtered and evaporated. The residue is chromatographed on silica gel, elution being carried out with 85/15 heptane/ethyl acetate.

930 mg of 1,5-bis(benzyloxy)-2-fluoro-4-aminobenzene are obtained.

Yield=61%.

c) 1,5-Bis(benzyloxy)-2-fluoro-4-iodobenzene 7 ml of 6M hydrochloric acid are added to a solution of 3.20 g (9.9 mmol, 1 eq) of 1,5-bis(benzyloxy)-2-fluoro-4-aminobenzene in 40 ml of N,N-dimethylformamide, cooled to 0° C. 683 mg (9.9 mmol, 1 eq) of sodium nitrite in solution in 7 ml of water are added and the reaction medium is stirred at 0° C. for 1 hour. 1.64 g (9.9 mmol, 1 eq) of potassium iodide in solution in 8 ml of water are added, followed by 190 mg (1.0 mmol, 0.1 eq) of copper iodide, and then the reaction medium is stirred at ambient temperature overnight. The reaction medium is treated with a saturated solution of ammonium chloride and extracted with ethyl acetate. The organic phases are combined, washed with a saturated solution of sodium chloride, dried over magnesium sulphate, filtered and evaporated. The residue is chromatographed on silica gel, elution being carried out with 75/25 heptane/dichloromethane. 3.59 g of 1,5-bis(benzyloxy)-2-fluoro-4-iodobenzene are obtained.

Yield=68%.

d) 4-(2,4-Bis(benzyloxy)-5-fluorophenyl)piperidine-1-carboxylic acid tert-butyl ester 4.0 ml (9.9 mmol, 1.2 eq) of 2.5M n-butyllithium in hexane are added to a solution of 3.59 g (8.26 mmol, 1 eq) of 1,5-bis(benzyloxy)-2-fluoro-4-iodobenzene in 40 ml of tetrahydrofuran, cooled to −70° C. The reaction medium is stirred at −70° C. for 25 minutes and 1.97 g (9.9 mmol, 1.2 eq) of 1-boc-4-piperidone in solution in 20 ml of tetrahydrofuran are added. The reaction medium is stirred at −70° C. for 1 hour and is then left to return to ambient temperature overnight. 30 ml of a saturated solution of ammonium chloride, to which 4 ml of 2M hydrochloric acid have been added, are added to the reaction medium, which is stirred for 20 minutes and is then extracted with ethyl acetate. The organic phases are combined, dried over magnesium sulphate and evaporated. The residue is chromatographed on silica gel, elution being carried out with 95/5 heptane/ethyl acetate then 75/25 heptane/ethyl acetate (with 0.1% of TEA).

860 mg of a mixture of 4-(2,4-bis(benzyloxy)-5-fluorophenyl)piperidine-1-carboxylic acid tert-butyl ester (25%) and of 1-boc-4-piperidone are obtained in the form of a yellow oil which crystallizes.

Yield=5%.

e) 4-(5-Fluoro-2,4-dihydroxyphenyl)-3,6-dihydro-2H-pyridine-1-carboxylic acid tert-butyl ester A mixture of 860 mg (0.42 mmol, 1 eq) of 4-(2,4-bis(benzyloxy)-5-fluorophenyl)piperidine-1-carboxylic acid tert-butyl ester at 35% in 10 ml of ethyl acetate, in the presence of 200 mg of palladium-on-charcoal at 10%, is stirred at ambient temperature under a hydrogen pressure of 5 bar for 17 hours. 5 ml of methanol are added and the reaction medium is stirred at ambient temperature under a hydrogen pressure of 5 bar for 29 hours. The reaction medium is filtered through filter paper and the filtrate is evaporated off. The residue is chromatographed on silica gel, elution being carried out with 60/40 heptane/ethyl acetate. 192 mg of 4-(5-fluoro-2,4-dihydroxyphenyl)-3,6-dihydro-2H-pyridine-1-carboxylic acid tert-butyl ester are obtained.

Yield=100%.

f) 4-(2,4-Bis(benzyloxy)-5-fluorophenyl)piperidine-1-carboxylic acid tert-butyl ester 241 mg (1.74 mmol, 3 eq) of potassium carbonate (325 mesh) are added to a solution of 181 mg (0.58 mmol, 1 eq) of 4-(5-fluoro-2,4-dihydroxyphenyl)piperidine-1-carboxylic acid tert-butyl ester in 3 ml of acetone. 152 µl (1.28 mmol, 2.2 eq) of benzyl bromide are added dropwise. The reaction medium is heated at 50° C. for 20 hours. The solvent is evaporated off and then the residue is taken up with a water/ethyl acetate mixture. The aqueous phase is extracted with ethyl acetate, and the organic phases are combined, washed with a solution of sodium hydrogen carbonate and then with a saturated solution of sodium chloride, dried over magnesium sulphate, filtered and evaporated. The residue is chromatographed on silica gel, elution being carried out with 85/15 heptane/ethyl acetate.

188 mg of 4-(2,4-bis(benzyloxy)-5-fluorophenyl)piperidine-1-carboxylic acid tert-butyl ester are obtained. Yield=66%.

g) 4-(2,4-Bis(benzyloxy)-5-fluorophenyl)piperidine

280 µl (3.7 mmol, 10 eq) of trifluoroacetic acid are added to a solution of 184 mg (0.37 mmol, 1 eq) of 4-(2,4-bis(benzyloxy)-5-fluorophenyl)piperidine-1-carboxylic acid tert-butyl ester in 3 ml of dichloromethane. The reaction medium is stirred at ambient temperature for 1 hour. The reaction medium is treated with 10 ml of water and then extracted with dichloromethane. The organic phases are combined, washed with a saturated solution of sodium hydrogen carbonate and then with a saturated solution of sodium chloride, dried over magnesium sulphate and evaporated. 150 mg of 4-(2,4-bis(benzyloxy)-5-fluorophenyl)piperidine are obtained. Yield=100%.

h) 4-(2,4-Bis(benzyloxy)-5-fluorophenyl)piperidine-1-carboxylic acid ((S)-1-phenylethyl)amide 65 µl (0.45 mmol, 1.2 eq) of (S)-(−)-phenylethyl isocyanate are added to a solution of 147 mg (0.37 mmol, 1 eq) of 4-(2,4-bis(benzyloxy)-5-fluorophenyl)piperidine in 3 ml of tetrahydrofuran in the presence of 64 µl (0.37 mmol, 1 eq) of dimethylethylamine. The reaction medium is stirred at ambient temperature for 50 minutes. The reaction is stopped by adding 5 ml of water, and then extracted with ethyl acetate. The organic phases are combined and dried over magnesium sulphate. The solvent is evaporated off and the residue is chromatographed on silica gel, elution being carried out with 60/40 heptane/ethyl acetate. 178 mg of 4-(2,4-bis(benzyloxy)-5-fluorophenyl)piperidine-1-carboxylic acid phenylamide are obtained. Yield=89%.

i) 4-(5-Fluoro-2,4-dihydroxyphenyl)piperidine-1-carboxylic acid ((S)-1-phenylethyl)amide A mixture of 174 mg (0.32 mmol, 1 eq) of 4-(2,4-bis(benzyloxy)-5-fluorophenyl)piperidine-1-carboxylic acid phenylamide in 1 ml of ethyl acetate and of 2 ml of methanol in the presence of 51 mg (30% by mass) of palladium-on-charcoal at 10% is stirred at ambient temperature under atmospheric hydrogen pressure for 8 hours. The reaction medium is filtered through filter paper and the filtrate is evaporated off. The residue is chromatographed on silica gel, elution being carried out with 30/70 heptane/ethyl acetate. 83 mg of 4-(5-fluoro-2,4-dihydroxyphenyl)piperidine-1-carboxylic acid ((S)-1-phenylethyl)amide are obtained. Yield=72%.
$^1$H NMR (DMSO, 400 MHz): 1.35-1.45 (m, 5H); 1.53 (m, 2H); 2.67 (t, J=13 Hz, 2H); 2.83 (m, 1H); 4.11 (d, J=12.3 Hz, 2H); 4.83 (m, 1H); 6.43 (d, J=8.0 Hz, 1H); 6.73 (m, 2H); 7.14-7.40 (m, 5H); 9.11 (s, 1H); 9.40 (s, 1H).
$^{13}$C NMR (DMSO, 100 MHz): 23.0, 31.6, 34.6, 44.2, 49.3, 104.5, 113.3 (d, J=19 Hz), 122.4, (d, J=5 Hz), 125.9, 126.1, 127.9, 142.4, 144.6 (d, J=228 Hz), 146.3, 150.4, 155.5.

EXAMPLE 47

(R)-1-[4-(2,4-Dihydroxyphenyl)piperidin-1-yl]-2-hydroxy-2-phenylethanone

In a manner analogous to Example 26, but using (R)-hydroxyphenylacetic acid, (R)-1-[4-(2,4-dihydroxyphenyl)piperidin-1-yl]-2-hydroxy-2-phenylethanone is obtained.
$^1$H NMR (DMSO, 400 MHz): (hindrance of rotation) 0.6 (m, 0.5H); 1.30-1.70 (m, 3.5H); 2.5-3 (m, 2H); 4.0 (m, 1H); 4.51 (m, 1H); 5.37-5.57 (m, 2H); 6.07 (m, 1H); 6.24 (m, 1H); 6.48 & 6.72 (2d, J=8.2 Hz, 1H); 7.29-7.38 (m, 5H); 8.98 (2s, 1H); 9.11 (2s, 1H)
$^{13}$C NMR (DMSO, 100 MHz): (hindrance of rotation) 30.9 & 31.4, 31.5 & 31.9, 34.1 & 34.4, 42.9, 45.2, 71.1, 102.4, 105.9, 121.8, 126.3, 126.4, 126.9, 127.5, 128.1, 128.3, 128.4, 128.9, 140.5, 155.1, 156.1, 170.0.

EXAMPLE 48

(S)-1-[4-(2,4-Dihydroxyphenyl)piperidin-1-yl]-2-hydroxy-2-phenylethanone

In a manner analogous to Example 26, but using (S)-hydroxyphenylacetic acid, (S)-1-[4-(2,4-dihydroxyphenyl)piperidin-1-yl]-2-hydroxy-2-phenylethanone is obtained.
$^1$H NMR (DMSO, 400 MHz): (hindrance of rotation) 0.6 (m, 0.5H); 1.30-1.70 (m, 3.5H); 2.5-3 (m, 2H); 4.0 (m, 1H); 4.51 (m, 1H); 5.37-5.57 (m, 2H); 6.07 (m, 1H); 6.24 (m, 1H); 6.48 & 6.72 (2d, J=8.2 Hz, 1H); 7.29-7.38 (m, 5H); 8.98 (2s, 1H); 9.11 (2s, 1H)
$^{13}$C NMR (DMSO, 100 MHz): (hindrance of rotation) 30.9 & 31.4, 31.5 & 31.9, 34.1 & 34.4, 42.9, 45.2, 71.1, 102.4, 105.9, 121.8, 126.3, 126.4, 126.9, 127.5, 128.1, 128.3, 128.4, 128.9, 140.5, 155.1, 156.1, 170.0.

EXAMPLE 49

(R)-1-[4-(2,4-Dihydroxyphenyl)piperidin-1-yl]-2-hydroxy-3-phenylpropan-1-one

In a manner analogous to Example 26, but using (R)-2-hydroxy-3-phenylpropionic acid, (R)-1-[4-(2,4-dihydroxyphenyl)piperidin-1-yl]-2-hydroxy-3-phenylpropan-1-one is obtained.
$^1$H NMR (DMSO, 400 MHz): (hindrance of rotation) 1.04-1.70 (m, 4H); 2.50-3.34 (m, 5H); 4.02 (m, 1H); 4.52 (m, 2H); 4.97 (m, 1H); 6.14 (d, J=8.2 Hz, 1H); 6.25 (m, 1H); 6.67 & 6.782 (2d, J=8.2 Hz, 1H); 7.14-7.28 (m, 5H); 8.97 (2s, 1H); 9.15 (2s, 1H).
$^{13}$C NMR (DMSO, 100 MHz): (hindrance of rotation) 31.6 & 31.7, 34.5 & 34.7, 40.3 & 40.6, 42.5, 45.6, 68.6 & 68.9, 102.5, 106.1, 122.1, 126.1, 126.8, 128.1, 129.6, 138.1 & 138.4, 155.3, 156.2, 171.0.

EXAMPLE 50

(S)-1-[4-(2,4-Dihydroxyphenyl)piperidin-1-yl]-2-hydroxy-3-phenylpropan-1-one

In a manner analogous to Example 26, but using (S)-2-hydroxy-3-phenylpropionic acid, (S)-1-[4-(2,4-dihydroxyphenyl)piperidin-1-yl]-2-hydroxy-3-phenylpropan-1-one is obtained.
$^1$H NMR (DMSO, 400 MHz): (hindrance of rotation) 1.04-1.70 (m, 4H); 2.50-3.34 (m, 5H); 4.02 (m, 1H); 4.52 (m, 2H); 4.97 (m, 1H); 6.14 (d, J=8.2 Hz, 1H); 6.25 (m, 1H); 6.67 & 6.782 (2d, J=8.2 Hz, 1H); 7.14-7.28 (m, 5H); 8.97 (2s, 1H); 9.15 (2s, 1H).
$^{13}$C NMR (DMSO, 100 MHz): (hindrance of rotation) 31.6 & 31.7, 34.5 & 34.7, 40.3 & 40.6, 42.5, 45.6, 68.6 & 68.9, 102.5, 106.1, 122.1, 126.1, 126.8, 128.1, 129.6, 138.1 & 138.4, 155.3, 156.2, 171.0.

EXAMPLE 51

Tyrosinase Activity Inhibition Assay

The activity of the inhibitors is measured using a lysate of B16F1 cells (murine melanoma line). In the presence of the L-tyrosine substrate, the tyrosinase present in these cells catalyses the hydroxylation of L-tyrosine to give L-DOPA and then the oxidation of the L-DOPA to give dopaquinone. In the presence of MBTH (3-methyl-2-benzothiazolinone hydrazone), the dopaquinone is trapped so as to form a pink complex which absorbs at 520 nm.

The B16F1 cells are cultured in DMEM medium+10% foetal calf serum+$10^{-9}$M α-MSH for 4 days at 37° C. under 7% $CO_2$. They are treated with trypsin, washed in PBS, counted and pelleted. The pellet is taken up at $10^7$ cells/ml in lysis buffer (10 mM sodium phosphate, pH 6.8—1% Igepal) and the suspension is treated with ultrasound for 10 seconds. After centrifugation for 30 minutes at 4000 rpm, the supernatant obtained constitutes the cell lysate used as tyrosinase source in the enzymatic assay.

The assays are carried out in duplicate in 384-well plates in a total volume of 50 μl. Each well contains:

- 40 μl of solution containing 1.25 mM L-tyrosine, 6.25 μM L-DOPA (cofactor) and 3.75 mM MBTH in buffer B (62.25 mM sodium phosphate, pH 6.8-2.5% dimethylformamide),
- 5 μl of inhibitor diluted in DMSO,
- 5 μl of cell lysate diluted to in 50 mM Tris HCl buffer, pH 7.5.

The plate is incubated at 37° C. and a spectrophotometric reading is carried out at 520 nm after 6 hours of incubation. In order to avoid any possible absorption of the products, the system uses corrected absorbance (absorbance at time 6 h-absorbance at time zero).

The inhibitors are assayed in terms of dose-response so as to calculate an $IC_{50}$ (dose which inhibits 50% of the enzymatic activity).

Several internal controls are added to each experiment:

- control for 100% activity: the 5 μl of inhibitor are replaced with 5 μl of DMSO,
- control for 50% activity: the 5 μl of inhibitor are replaced with 5 μl of phenylthiourea at 300 μM in DMSO,
- control for 0% activity: the L-tyrosine substrate is replaced with buffer B.

The results obtained for the compounds of the invention are shown in Table A:

TABLE A

| Name | Structure | Tyrosine hydroxylase/ Dopa oxidase $IC_{50}$ (μM) |
|---|---|---|
| 4-Butylresorcinol (Rucinol) | 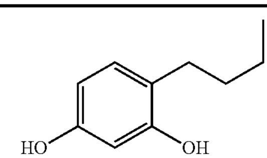 | 3 |
| Compound 48 | 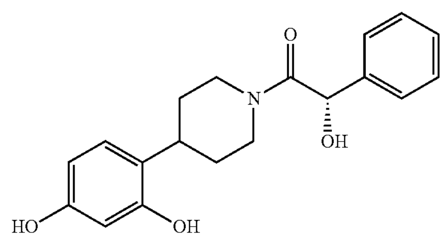 | 0.2 |
| Compound 24 | 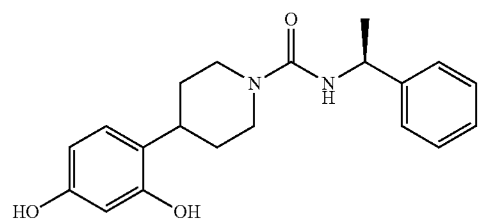 | 0.15 |

EXAMPLE 52

Melanogenesis Inhibition Assay

The inhibition of melanogenesis is measured in MNT1 human melanoma cells according to a protocol adapted from Reigner et al., Cell Mol Biol (1999) 45: 969-980. The assay is based on the concomitant incorporation of 2 radiolabelled tracers: $^{14}$C-thiouracil is incorporated into the neosynthesized melanin and reflects melanogenesis, whereas $^3$H-leucine is incorporated into the proteins and reflects cell viability and, consequently, the toxicity of the compounds tested.

The MNT1 cells are seeded into 96-well plates in the presence of the test compounds and of the radioisotopes. After incubation for 24 h at 37° C., the cells are washed and the amount of the 2 radioisotopes is measured. The test compounds are evaluated in terms of dose-response so as to calculate an IC$_{50}$ for inhibition of melanogenesis on the basis of the $^{14}$C incorporation which is standardized through the $^3$H incorporation. An IC$_{50}$ for cell toxicity is also calculated on the basis of the $^3$H incorporation.

This assay therefore makes it possible to distinguish the products that specifically inhibit melanogenesis from those which are cytotoxic to melanocytes.

| Name | Formula | IC$_{50}$ melanogenesis | IC$_{50}$ toxicity |
|---|---|---|---|
| 4-Butyl-resorcinol (Rucinol) | 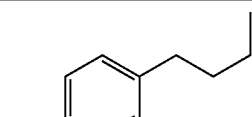 | 15 μM | 55 μM |
| Compound 48 | 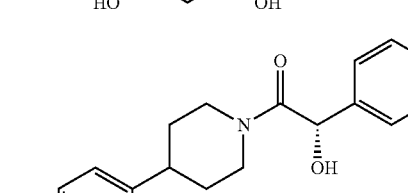 | 0.7 μM | >999 μM |
| Compound 24 | 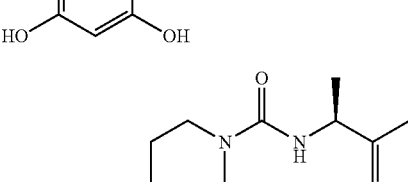 | 0.3 μM | >999 μM |

EXAMPLE 53

Formulations

This example illustrates various formulations based on the compounds according to the invention.

Topically

| (a) Ointment | |
|---|---|
| Compound 16 | 0.020 g |
| Isopropyl myristate | 81.700 g |
| Liquid petroleum jelly | 9.100 g |
| Silica (Aerosil 200) | 9.180 g |
| (b) Ointment | |
| Compound 6 | 0.300 g |
| White petroleum jelly, pharmaceutical grade | qs 100 g |
| (c) Nonionic water-in-oil cream | |
| Compound 16 | 0.100 g |
| Mixture of emulsive lanolin alcohols, of waxes and of oils (Anhydrous eucerin) | 39.900 g |
| Methyl para-hydroxybenzoate | 0.075 g |
| Propyl para-hydroxybenzoate | 0.075 g |
| Sterile demineralized water | qs 100 g |
| (d) Lotion | |
| Compound 6 | 0.100 g |
| Polyethylene glycol (PEG 400) | 69.900 g |
| 95% ethanol | 30.000 g |
| (e) Hydrophobic ointment | |
| Compound 22 | 0.300 g |
| Isopropyl myristate | 36.400 g |
| Silicone oil (Rhodorsil 47 V 300) | 36.400 g |
| Beeswax | 13.600 g |
| Silicone oil (Abil 300,000 cst) | qs 100 g |
| (f) Nonionic oil-in-water cream | |
| Compound 4 | 1.000 g |
| Cetyl alcohol | 4.000 g |
| Glyceryl monostearate | 2.500 g |
| PEG 50 stearate | 2.500 g |
| Shea butter | 9.200 g |
| Propylene glycol | 2.000 g |
| Methyl para-hydroxybenzoate | 0.075 g |
| Propyl para-hydroxybenzoate | 0.075 g |
| Sterile demineralized water | qs 100 g |

The invention claimed is:
1. A compound of general formula (I) below:

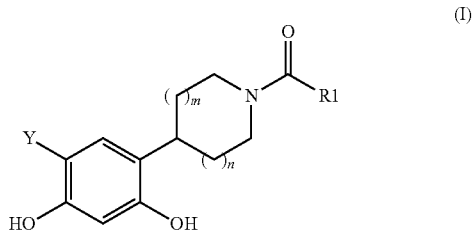

in which:
R1 represents:
  a $C_1$-$C_5$ alkyl radical,
  a $C_3$-$C_6$ cycloalkyl radical,
  an aryl radical,
  a substituted aryl radical,
  an aralkyl radical,
  a $C_1$-$C_5$ alkoxy radical,
  an amino radical corresponding to structure (a):

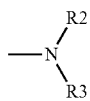
(a)

in which R2 represents:
    a hydrogen,
    a $C_1$-$C_5$ alkyl radical,
    a $C_3$-$C_6$ cycloalkyl radical,
    an aryl radical,
    a substituted aryl radical,
    a pyridyl radical,
    an aralkyl radical,
    a radical corresponding to structure (b):

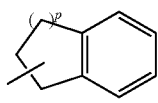
(b)

in which p can have the value 1 or 2,
    a radical corresponding to structure (c):

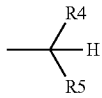
(c)

in which R4 represents:
      a carboxymethyl —COOCH$_3$ or carboxyethyl —COOEt radical,
      a $C_1$-$C_3$ alkyl radical,
      a hydrogen,
    and R5 represents:
      a substituted or unsubstituted aryl radical,
      a $C_3$-$C_6$ cycloalkyl radical,
      a pyridyl,
    and R3 represents:
      a hydrogen,
      a $C_1$-$C_5$ alkyl radical;
  or R1 may also represent a radical corresponding to formula (d):

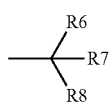
(d)

in which R6 represents:
    a hydrogen,
    a $C_1$-$C_5$ alkyl radical,
    a $C_3$-$C_6$ cycloalkyl radical,
    an aryl radical,
    a substituted aryl radical,
    a pyridyl radical,
    an aralkyl radical,
  R7 represents:
    a hydrogen,
    a $C_1$-$C_5$ alkyl radical,
  and R8 represents:
    a hydrogen,
    a hydroxyl,
    an amino radical,
    a $C_1$-$C_3$ alkoxy radical;
  Y represents a hydrogen or a fluorine, and
  m and n can have the value 0, 1 or 2,
  and also salts of the compounds of formula (I), and enantiomer forms thereof.

2. The compound according to claim 1, wherein the compound is in the form of a salt formed with a base selected from the group consisting of an organic base and inorganic base.

3. The compound according to claim 1, wherein:
  R1 represents an aralkyl radical or an amino radical corresponding to structure (a):

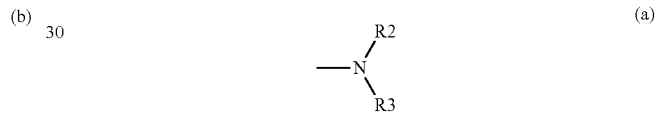
(a)

in which R2 represents:
    a $C_1$-$C_5$ alkyl radical,
    an aralkyl radical or
    a radical corresponding to structure (d):

(d)

in which R4 represents:
    a carboxymethyl —COOCH$_3$ or carboxyethyl —COOEt radical,
    a $C_1$-$C_3$ alkyl radical,
  and R5 represents:
    a substituted or unsubstituted aryl radical,
  and R3 represents a hydrogen,
  Y represents a hydrogen atom or a fluorine,
  m=1 and n=1,
  and also salts of the compounds of general formula (I), and enantiomer forms thereof.

4. The compound according to claim 1, wherein the compound is selected from the group consisting of:
  1: 3-(2,4-dihydroxyphenyl)azetidine-1-carboxylic acid tert-butyl ester;
  2: [3-(2,4-dihydroxyphenyl)azetidin-1-yl]phenylmethanone;
  3: 3-(2,4-dihydroxyphenyl)azetidine-1-carboxylic acid pentylamide;
  4: 3-(2,4-dihydroxyphenyl)pyrrolidine-1-carboxylic acid tert-butyl ester;

5: 3-(2,4-dihydroxyphenyl)pyrrolidine-1-carboxylic acid isobutyl ester;
6: 3-(2,4-dihydroxyphenyl)pyrrolidine-1-carboxylic acid cyclohexylamide;
7: 3-(2,4-dihydroxyphenyl)pyrrolidine-1-carboxylic acid phenylamide;
8: 3-(2,4-dihydroxyphenyl)pyrrolidine-1-carboxylic acid (4-fluorophenyl)amide;
9: 3-(2,4-dihydroxyphenyl)pyrrolidine-1-carboxylic acid (4-trifluoromethylphenyl)amide;
10: 4-(2,4-dihydroxyphenyl)piperidine-1-carboxylic acid ethyl ester;
11: [4-(2,4-dihydroxyphenyl)piperidin-1-yl]phenyl-methanone;
12: 4-(2,4-dihydroxyphenyl)piperidine-1-carboxylic acid butylamide;
13: 4-(2,4-dihydroxyphenyl)piperidine-1-carboxylic acid propylamide;
14: 1-[4-(2,4-dihydroxyphenyl)piperidin-1-yl]butan-1-one;
15: 1-[4-(2,4-dihydroxyphenyl)piperidin-1-yl]-2-methyl-propan-1-one;
16: 4-(2,4-dihydroxyphenyl)piperidine-1-carboxylic acid phenylamide;
17: 4-(2,4-dihydroxyphenyl)piperidine-1-carboxylic acid (4-fluorophenyl)amide;
18: 4-(2,4-dihydroxyphenyl)piperidine-1-carboxylic acid p-tolylamide;
19: 4-(2,4-dihydroxyphenyl)piperidine-1-carboxylic acid phenethylamide;
20: 4-(2,4-dihydroxyphenyl)piperidine-1-carboxylic acid (3-fluorophenyl)amide;
21: 4-(2,4-dihydroxyphenyl)piperidine-1-carboxylic acid ((R)-1-phenylethyl)amide;
22: 4-(2,4-dihydroxyphenyl)piperidine-1-carboxylic acid methylphenylamide;
23: 4-(2,4-dihydroxyphenyl)piperidine-1-carboxylic acid pyridin-2-ylamide;
24: 4-(2,4-dihydroxyphenyl)piperidine-1-carboxylic acid ((S)-1-phenylethyl)amide;
25: 4-(2,4-dihydroxyphenyl)piperidine-1-carboxylic acid ((S)-1-phenylpropyl)amide;
26: (R)-2-amino-1-[4-(2,4-dihydroxyphenyl)piperidin-1-yl]-3-phenylpropan-1-one;
27: 1-[4-(2,4-dihydroxyphenyl)piperidin-1-yl]-3-phenyl-propan-1-one;
28: 4-(2,4-dihydroxyphenyl)piperidine-1-carboxylic acid 2-fluorobenzylamide;
29: 4-(2,4-dihydroxyphenyl)piperidine-1-carboxylic acid 3-fluorobenzylamide;
30: 4-(2,4-dihydroxyphenyl)piperidine-1-carboxylic acid 4-fluorobenzylamide;
31: 4-(2,4-dihydroxyphenyl)piperidine-1-carboxylic acid benzylamide;
32: 4-(2,4-dihydroxyphenyl)piperidine-1-carboxylic acid 2-methylbenzylamide;
33: 4-(2,4-dihydroxyphenyl)piperidine-1-carboxylic acid 3-methylbenzylamide;
34: 4-(2,4-dihydroxyphenyl)piperidine-1-carboxylic acid 4-methylbenzylamide;
35: 4-(2,4-dihydroxyphenyl)piperidine-1-carboxylic acid 2-methoxybenzylamide;
36: 4-(2,4-dihydroxyphenyl)piperidine-1-carboxylic acid 3-methoxybenzylamide;
37: 4-(2,4-dihydroxyphenyl)piperidine-1-carboxylic acid 4-methoxybenzylamide;
38: 4-(2,4-dihydroxyphenyl)piperidine-1-carboxylic acid ((S)-1-p-tolylethyl)amide;
39: 4-(2,4-dihydroxyphenyl)piperidine-1-carboxylic acid [(S)-1-(4-fluorophenyl)ethyl]amide;
40: 4-(2,4-dihydroxyphenyl)piperidine-1-carboxylic acid (S)-indan-1-ylamide;
41: 4-(2,4-dihydroxyphenyl)piperidine-1-carboxylic acid ((S)-1-naphthalen-1-ylethyl)amide;
42: 4-(2,4-dihydroxyphenyl)piperidine-1-carboxylic acid ((S)-1-naphthalen-2-ylethyl)amide;
43: 4-(2,4-dihydroxyphenyl)piperidine-1-carboxylic acid [(S)-1-(4-methoxyphenyl)ethyl]amide;
44: 4-(2,4-dihydroxyphenyl)piperidine-1-carboxylic acid [(S)-1-(3-methoxyphenyl)ethyl]amide;
45: (S)-2-amino-1-[4-(2,4-dihydroxyphenyl)piperidin-1-yl]-3-phenylpropan-1-one;
46: 4-(5-fluoro-2,4-dihydroxyphenyl)piperidine-1-carboxylic acid ((S)-1-phenylethyl)amide;
47: (R)-1-[4-(2,4-dihydroxyphenyl)piperidin-1-yl]-2-hydroxy-2-phenylethanone;
48: (S)-1-[4-(2,4-dihydroxyphenyl)piperidin-1-yl]-2-hydroxy-2-phenylethanone;
49: (R)-1-[4-(2,4-dihydroxyphenyl)piperidin-1-yl]-2-hydroxy-3-phenylpropan-1-one;
50: (S)-1-[4-(2,4-dihydroxyphenyl)piperidin-1-yl]-2-hydroxy-3-phenylpropan-1-one;
51: (R)-2-amino-1-[4-(2,4-dihydroxyphenyl)piperidin-1-yl]-2-(4-fluorophenyl)ethanone;
52: (R)-2-amino-1-[4-(2,4-dihydroxyphenyl)piperidin-1-yl]-2-phenylethanone;
53: (S)-2-amino-1-[4-(2,4-dihydroxyphenyl)piperidin-1-yl]-2-phenylethanone;
54: (R)-2-amino-1-[4-(2,4-dihydroxyphenyl)piperidin-1-yl]-2-(4-trifluoromethylphenyl)ethanone;
55: 2-amino-1-[4-(2,4-dihydroxyphenyl)piperidin-1-yl]-2-phenylbutan-1-one;
56: (S)-1-[4-(2,4-dihydroxyphenyl)piperidin-1-yl]-2-methoxy-2-phenylethanone;
57: 4-(2,4-dihydroxyphenyl)piperidine-1-carboxylic acid ((S)-1-cyclohexylethyl)amide;
58: 4-(2,4-dihydroxyphenyl)piperidine-1-carboxylic acid (1,2,3,4-tetrahydronaphthalen-1-yl)amide;
59: (R)-{[4-(2,4-dihydroxyphenyl)piperidine-1-carbonyl]amino}phenylacetic acid methyl ester;
60: 4-(2,4-dihydroxyphenyl)piperidine-1-carboxylic acid (pyridin-3-ylmethyl)amide;
61: 4-(2,4-dihydroxyphenyl)piperidine-1-carboxylic acid (pyridin-4-ylmethyl)amide;
62: 4-(5-fluoro-2,4-dihydroxyphenyl)piperidine-1-carboxylic acid benzylamide;
63: 4-(5-fluoro-2,4-dihydroxyphenyl)piperidine-1-carboxylic acid butylamide;
64: 4-(5-fluoro-2,4-dihydroxyphenyl)piperidine-1-carboxylic acid (3-fluorophenyl)amide;
65: 4-(5-fluoro-2,4-dihydroxyphenyl)piperidine-1-carboxylic acid phenethylamide;
66: (R)-{[4-(5-fluoro-2,4-dihydroxyphenyl)piperidine-1-carbonyl]amino}phenylacetic acid methyl ester;
67: 4-(5-fluoro-2,4-dihydroxyphenyl)piperidine-1-carboxylic acid (S)-indan-1-ylamide;
68: 4-(5-fluoro-2,4-dihydroxyphenyl)piperidine-1-carboxylic acid [(S)-1-(4-methoxyphenyl)ethyl]amide;
69: 4-(5-fluoro-2,4-dihydroxyphenyl)piperidine-1-carboxylic acid ((S)-1-cyclohexylethyl)amide;
70: (R)-1-[4-(5-fluoro-2,4-dihydroxyphenyl)piperidin-1-yl]-2-hydroxy-2-phenylethanone;

71: (S)-1-[4-(5-fluoro-2,4-dihydroxyphenyl)piperidin-1-yl]-2-hydroxy-2-phenylethanone;
72: (R)-2-amino-1-[4-(5-fluoro-2,4-dihydroxyphenyl)piperidin-1-yl]-2-phenylethanone;
73: (S)-2-amino-1-[4-(5-fluoro-2,4-dihydroxyphenyl)piperidin-1-yl]-2-phenylethanone;
74: (R)-1-[4-(5-fluoro-2,4-dihydroxyphenyl)piperidin-1-yl]-2-hydroxy-2-phenylpropan-1-one;
75: (S)-1-[4-(5-fluoro-2,4-dihydroxyphenyl)piperidin-1-yl]-2-hydroxy-2-phenylpropan-1-one;
76: (R)-1-[4-(2,4-dihydroxyphenyl)piperidin-1-yl]-2-hydroxy-2-phenylpropan-1-one;
77: (S)-1-[4-(2,4-dihydroxyphenyl)piperidin-1-yl]-2-hydroxy-2-phenylpropan-1-one;
78: (R)-{[4-(2,4-dihydroxyphenyl)piperidine-1-carbonyl]amino}-(4-fluorophenyl)acetic acid methyl ester;
79: (S)-{[4-(2,4-dihydroxyphenyl)piperidine-1-carbonyl]amino}-(4-fluorophenyl)acetic acid methyl ester;
80: (R)-1-[4-(2,4-dihydroxyphenyl)piperidin-1-yl]-2-hydroxy-2-methyl-3-phenylpropan-1-one;
81: (S)-1-[4-(2,4-dihydroxyphenyl)piperidin-1-yl]-2-hydroxy-2-methyl-3-phenylpropan-1-one;
82: 4-(5-fluoro-2,4-dihydroxyphenyl)piperidine-1-carboxylic acid (pyridin-3-ylmethyl)amide;
83: 4-(5-fluoro-2,4-dihydroxyphenyl)piperidine-1-carboxylic acid (pyridin-4-ylmethyl)amide;
84: (5-fluoro-2,4-dihydroxyphenyl)piperidine-1-carboxylic acid ((R)-1-phenylethyl)amide;
85: (R)-1-[4-(2,4-dihydroxyphenyl)piperidin-1-yl]-2-hydroxy-2-phenylbutan-1-one;
86: (S)-1-[4-(2,4-dihydroxyphenyl)piperidin-1-yl]-2-hydroxy-2-phenylbutan-1-one;
87: (S)-1-[4-(2,4-dihydroxyphenyl)piperidin-1-yl]-2-(4-fluorophenyl)-2-hydroxyethanone;
88: (R)-1-[4-(2,4-dihydroxyphenyl)piperidin-1-yl]-2-(4-fluorophenyl)-2-hydroxyethanone;
89: (S)-1-[4-(2,4-dihydroxyphenyl)piperidin-1-yl]-2-hydroxy-2-(3-methoxyphenyl)ethanone;
90: (R)-1-[4-(2,4-dihydroxyphenyl)piperidin-1-yl]-2-hydroxy-2-(3-methoxyphenyl)ethanone;
91: 4-(5-fluoro-2,4-dihydroxyphenyl)piperidine-1-carboxylic acid cyclohexylmethylamide;
92: 4-(2,4-dihydroxyphenyl)piperidine-1-carboxylic acid cyclohexylmethylamide;
93: 4-(2,4-dihydroxyphenyl)piperidine-1-carboxylic acid (2-ethylbutyl)amide;
94: 4-(5-fluoro-2,4-dihydroxyphenyl)piperidine-1-carboxylic acid (2-ethylbutyl)amide;
95: 4-(2,4-dihydroxyphenyl)piperidine-1-carboxylic acid cyclopentylmethylamide;
96: 4-(5-fluoro-2,4-dihydroxyphenyl)piperidine-1-carboxylic acid cyclopentylmethylamide;
97: 4-(2,4-dihydroxyphenyl)piperidine-1-carboxylic acid (6-methylpyridin-3-ylmethyl)amide;
98: 4-(2,4-dihydroxyphenyl)piperidine-1-carboxylic acid (4-methylpyridin-3-ylmethyl)amide;
99: 4-(2,4-dihydroxyphenyl)piperidine-1-carboxylic acid (5-methylpyridin-3-ylmethyl)amide;
100: 4-(2,4-dihydroxyphenyl)piperidine-1-carboxylic acid (2-methylpyridin-3-ylmethyl)amide;
101: 4-(2,4-dihydroxyphenyl)piperidine-1-carboxylic acid (2,6-dimethylpyridin-4-ylmethyl)amide;
102: 4-(2,4-dihydroxyphenyl)piperidine-1-carboxylic acid (2-pyridin-2-ylethyl)amide;
103: 4-(2,4-dihydroxyphenyl)piperidine-1-carboxylic acid (2-pyridin-3-ylethyl)amide; and
104: 4-(2,4-dihydroxyphenyl)piperidine-1-carboxylic acid (2-pyridin-4-ylethyl)amide.

\* \* \* \* \*